United States Patent [19]

Curtiss et al.

[11] Patent Number: 5,055,396

[45] Date of Patent: Oct. 8, 1991

[54] DIAGNOSTIC METHODS AND SYSTEMS FOR QUANTIFYING APO AI

[75] Inventors: Linda K. Curtiss, San Diego; Richard S. Smith, Del Mar, both of Calif.

[73] Assignee: Scripps Clinic and Research Foundation, La Jolla, Calif.

[21] Appl. No.: 116,248

[22] Filed: Nov. 2, 1987

[51] Int. Cl.$^5$ .................. G07N 33/53; C12N 5/00; G01N 33/543

[52] U.S. Cl. ................... 435/7.93; 530/326; 530/327; 530/387; 530/806; 435/240.27; 435/810; 435/7.92; 436/548; 436/518; 436/808; 935/96; 935/110

[58] Field of Search ............. 530/326, 327, 806, 387; 435/240.27, 810, 7; 436/548, 518, 808; 935/96, 110

[56] References Cited

U.S. PATENT DOCUMENTS 4,327,075 4/1982 Lüning .................. 424/12

OTHER PUBLICATIONS

L. K. Curtiss, Immunochemical Heterogeneity of Human Plasma High Density Lipoproteins, vol. 260, No. 5, Mar. 10, 1985, pp. 2982–2993, The Journal of Biological Chemistry.
Curtiss et al., *J. Biol. Chem.*, 263:13779–13785 (1988).

*Primary Examiner*—Christine Nucker
*Assistant Examiner*—Laurie A. Scheiner
*Attorney, Agent, or Firm*—Dressler, Goldsmith, Shore, Sutker & Milnamow, Ltd.

[57] ABSTRACT

The present invention describes a monoclonal antibody that is directed against an Apo AI/HLD epitope whose expression is substantially unaffected by deamidation. Also disclosed is a polypeptide capable of immunologically mimicking an Apo AI/HLD epitope whose expression is substantially unaffected by deamidation. Diagnostic systems and methods for determining the amount of Apo AI in a vascular fluid sample using a disclosed monoclonal antibody and/or a disclosed polypeptide are also described.

15 Claims, 9 Drawing Sheets

DIAGNOSTIC METHODS AND SYSTEMS FOR QUANTIFYING APO AI

TECHNICAL FIELD

The present invention relates to antibodies and polypeptides useful for immunologically determining the amount of Apo AI in a vascular fluid sample.

BACKGROUND

Lipoproteins are the primary carriers of plasma cholesterol. They are micellar lipid-protein complexes (particles) having a surface film, comprised of one or more proteins associated with polar lipids, that surrounds a cholesterol-containing core. Lipoproteins were originally classified based on their buoyant densities as measured by ultracentrifugation. Accordingly, four major density classes have been recognized: chylomicrons, very low-density lipoproteins (VLDL), low-density lipoproteins LDL and high-density lipoproteins (HDL).

Many studies have now established an inverse correlation between plasma HDL cholesterol levels and risk of coronary artery disease (CAD). That is, elevated levels of plasma cholesterol found in HDL particles correlate with a reduced risk of CAD.

Similarly, many studies have now shown that plasma levels of apolipoprotein AI (Apo AI), the major protein component of HDL, are also inversely related to the risk of CAD. In addition, Weisweiler et al., Clin. Chem., 27:348 (1981) have reported that knowledge of Apo AI levels may add to the predictive value of HDL cholesterol.

Because of its inverse correlation with CAD, there has been an extensive amount of research into the structure and function of Apo AI in lipid metabolism. Functionally, Apo AI is now believed to mediate the removal of cholesterol from tissues and to activate LCAT.

Structurally, purified Apo AI has been described as containing a high proportion (55%) of alpha-helix, which increases to 70% when it is associated with phospholipids as in the HDL particle. The lipid binding properties of Apo AI appear to be a function of a series of tandemly repeated segments of 22 amino acid residues punctuated mostly by proline residues that are alpha-helical and amphophilic.

The amino acid residue sequence of Apo AI, determined by Edman degradation of cyanogen bromide- and trypsin-fragments of intact Apo AI, has been described by Brewer et al., Biochem. Biophys. Res. Comm., 80:623-630 (1978). According to Brewer et al., cyanogen bromide (CNBr) cleavage of Apo AI produced four major fragments, designated CNBr1, CNBr2, CNBr3 and CNBr4, in order of their occurrence along the Apo AI sequence from amino-terminus to carboxy-terminus. Because it is of particular interest to the present invention, the amino acid residue sequence of the region of Apo AI from which CNBr2 is produced is illustrated in FIG. 1, along with the positions of the various fragments produced by trypsin cleavage of CNBr2.

It should be noted that CNBr2, like CNBr1, CNBr3 and CNBr4, is a polypeptide having homoserine lactone at its carboxy terminus as a result of the methione residue at that position being degraded during the CNBr cleavage process.

Immunochemical characterization of native Apo AI, i.e., Apo AI as it is found on HDL particles, has been problematical because it is antigenically heterogeneous and unstable. The antigenic heterogeneity of Apo AI appears to be the result of some epitopes being masked by lipids in the intact HDL or the antibody-binding ability of some epitopes being dependent on conformations of Apo AI as affected by lipids or other HDL associated proteins. The antigenic instability of Apo AI, as manifest by its changing immunoreactivity over time with defined antisera, appears to be due to such phenomena as self association and deamidation, both of which have been shown to occur in vitro.

Of particular interest to the present invention is deamidation, which, with Apo AI, results in the conversion of asparagine and glutamine residues into aspartic acid and glutamic acid, respectively. Deamidation of Apo AI can be accomplished in vitro by treatment with sodium hydroxide (NaOH), and is evidenced by its acquisition of a net negative charge, i.e., net increase in isoelectric point. See Curtiss et al., Proceeding of the Workshop on Lipoprotein Heterogeniety, Ed. by Lippel, National Institutes of Health Publication No. 87-2646, P. 363-377 (1987). According to Milthorp et al., Arterio., 6:285-296 (1986), the effects of storage and NaOH treatment on native Apo AI immunoreactivity are similar but not analogous, suggesting that while loss of Apo AI immunoreactivity during storage is due in large part to deamidation, more may be involved.

The antigenic heterogeneity and instability of Apo AI has made it difficult to produce assay systems for quantifying Apo AI in patient vascular fluid samples. This is because, inter alia, such systems require a reference material (standard) whose immunoreactivity for the system's primary anti-Apo AI antibody is consistent, at the very least, and preferably equivalent to that of the Apo AI in the patient's sample.

Recently, efforts at overcoming problems associated with the antigenic heterogenicity and instability of Apo AI have focused on using monoclonal antibodies (MAB) to identify epitopes on native Apo AI whose expression is consistent or "conserved" under specific isolation and storage conditions. Such epitopes, referred to herein as "conserved native epitopes", are further defined as Apo AI epitopes whose expression on HDL is not significantly affected, i.e., not significantly increased or decreased, as a result of processing or storage that results in deamidation.

An exemplary conserved native Apo AI epitope, designated epitope A, has been defined by Milthorpe et al., Arterio., 6:285-296 (1986) as being that portion of Apo AI CNBr1 that immunoreacts with MAB 4H1. According to Milthorp et al., the expression of epitope A remains constant overtime in patient serum samples stored at temperatures ranging from 4 degrees C. to −80 degrees C. This was in contrast to epitopes designated C, C' and C'', all located in the CNBr2 region of Apo AI, and all of which were found to be "nonconserved" epitopes, i.e., epitopes whose expression was significantly increased or reduced upon storage at a similar range of temperatures.

BRIEF SUMMARY OF THE INVENTION

A native conserved Apo AI epitope whose expression is substantially unaffected by deamidation has now been discovered. In addition, a polypeptide capable of immunologically mimicking that epitope has been discovered. Thus, the present invention contemplates an Apo AI polypeptide consisting essentially of no more than 25 amino acid residues and having as a part of its amino acid residue sequence a sequence represented by the formula:

—AKVQPYLDDFQ—

Also contemplated is a monoclonal antibody containing anti-Apo AI antibody molecules that immunoreact with:
(a) Apo AI/HDL
(b) isolated Apo AI
(c) deamidated Apo AI/HDL
(d) Apo AI CNBr2, and
(e) the polypeptide LEEVKAKVQPYLDDFQ,
but do not immunoreact with:
(f) Apo AI CNBr1,
(g) Apo AI CNBr3,
(h) Apo AI CNBr4,
(i) the polypeptide LEEVKAKVQYLDDFQ, and
(j) the polypeptide LEEVKAKVQGYLDDFQ.

In another embodiment, the present invention contemplates a diagnostic system, in kit form, that includes, in an amount sufficient to perform at least one assay, an Apo AI polypeptide represented by a formula selected from the group consisting of:
(a) AKVQPYLDDFQ,
(b) LEEVKAKVQPYLDDFQ,
(c) LEEVKAKVQPYLDDFQKKWQEE, and
(d) KDLEEVKAKVQPYLDDFQ.

A diagnostic system, in kit form, that includes, in an amount sufficient to perform at least one assay, a monoclonal antibody containing anti-Apo AI antibody molecules that immunoreact with:
(a) Apo AI/HDL
(b) isolated Apo AI
(c) deamidated Apo AI/HDL
(d) Apo AI CNBr2, and
(e) the polypeptide LEEVKAKVQPYLDDFQ,
but do not immunoreact with:
(f) Apo AI CNBr1,
(g) Apo AI CNBr3,
(h) Apo AI CNBr4,
(i) the polypeptide LEEVKAKVQYLDDFQ, and
(j) the polypeptide LEEVKAKVQGYLDDFQ, is also contemplated.

Still further contemplated is a method of assaying the amount of Apo AI in a vascular fluid sample comprising the steps of:
(a) forming an immunoreaction admixture by admixing a vascular fluid sample with:
  (i) an anti-Apo AI monoclonal antibody produced by the hybridoma having ATCC designation HB9570, and
  (ii) an Apo AI polypeptide selected from the group consisting of:
    (a) AKVQPYLDDFQ,
    (b) LEEVKAKVQPYLDDFQ,
    (c) LEEVKAKVQPYLDDFQKKWQEE, and
    (d) KDLEEVKAKVQPYLDDFQ;
(b) maintaining said immunoreaction admixture for a time period sufficient to form an Apo AI-containing immunoreaction product, and
(c) determining the amount of product formed in step (b).

BRIEF DESCRIPTION OF THE DRAWINGS

In the drawings forming a portion of this disclosure.

DETAILED DESCRIPTION OF THE INVENTION

A. Definitions

Figure 1:
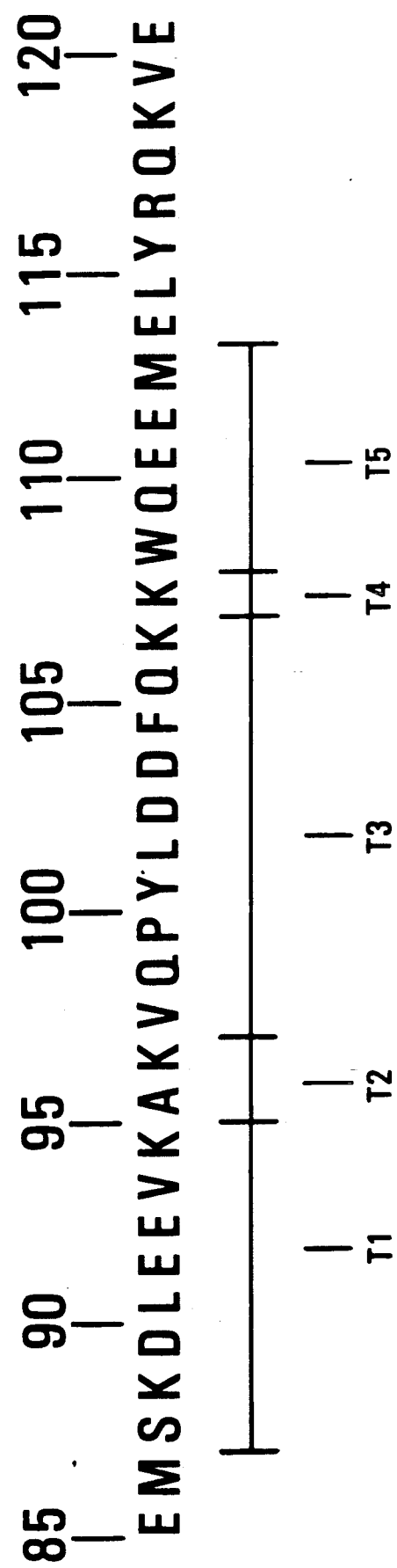
FIG. 1 illustrates the amino acid residue sequence of Apo AI, as reported by Brewer et al., *Biochem. Biophys. Res. Comm.*, 80:623-630 (1978), from residue positions 85 through 120. Apo AI CNBr2, which is formed by cleavage at the methionine (M) residues located at positions 86 and 112, corresponds in sequence to positions 87 through 111 with the carboxy terminal methionine being converted to homoserine lactone. The positions of the 5 fragments produced upon trypsin cleavage of CNBr2, designated T1 through T5, are also indicated.

Amino Acid: All amino acid residues identified herein are in the natural L-configuration. In keeping with standard polypeptide nomenclature, *J. Biol. Chem.*, 243:3557-59, (1969), abbreviations for amino acid residues are as shown in the following Table of Correspondence:

| TABLE OF CORRESPONDENCE | | |
|---|---|---|
| SYMBOL | | |
| 1-Letter | 3-Letter | AMINO ACID |
| Y | Tyr | L-tyrosine |
| G | Gly | glycine |
| F | Phe | L-phenylalanine |
| M | Met | L-methionine |
| A | Ala | L-alanine |
| S | Ser | L-serine |
| I | Ile | L-isoleucine |
| L | Leu | L-leucine |
| T | Thr | L-threonine |
| V | Val | L-valine |
| P | Pro | L-proline |
| K | Lys | L-lysine |
| H | His | L-histidine |
| Q | Gln | L-glutamine |
| E | Glu | L-glutamic acid |
| W | Trp | L-tryptophan |
| R | Arg | L-arginine |
| D | Asp | L-aspartic acid |
| N | Asn | L-asparagine |
| C | Cys | L-cysteine |

It should be noted that all amino acid residue sequences are represented herein by formulae whose left to right orientation is in the conventional direction of amino-terminus to carboxy-terminus. Furthermore, it should be noted that a dash at the beginning or end of an amino acid residue sequence indicates a bond to a further sequence of one or more amino acid residues up to a total of about fifty residues in the polypeptide chain.

Apo AI/HDL: Designates Apo AI when it is present on HDL particles.

Delipidated Apo AI: Refers to Apo AI that is substantially free of associated lipids.

Isolated Apo AI: Designates Apo AI that is substantially free of both associated lipids and other proteins, such as those, like Apo AII, that are typically found on HDL in addition to Apo AI.

Polypeptide and Peptide: Polypeptide and peptide are terms used interchangeably herein to designate a linear series of no more than 20 amino acid residues connected one to the other by peptide bonds between the alpha-amino and carboxy groups of adjacent residues.

Protein: Protein is a term used herein to designate a linear series of greater than 20 amino acid residues connected one to the other as in a polypeptide.

B. Polypeptides

As used herein, the phrase "Apo AI polypeptide" refers to a polypeptide whose amino acid residue sequence is homologous (similar in structure) to a portion of the Apo AI molecule.

In one embodiment, an Apo AI polypeptide of the present invention consists essentially of at least about 9 and no more than about 40 amino acid residues and has as a portion of its sequence a sequence represented by the formula:

AKVQPYLDDFQ, and wherein said polypeptide is free of homoserine lactone.

In another embodiment, an Apo AI polypeptide of this invention consists essentially of at least about 9 and no more than 25, preferably no more than about 20 amino acid residues and has as a portion its sequence a sequence represented by the formula:

AKVQPYLDDFQ

Preferred Apo AI polypeptides are shown in Table 1.

TABLE 1

| Designation | Amino Acid Residue Sequence |
|---|---|
| AI90-105 | LEEVKAKVQPYLDDFQ |
| AI90-111 | LEEVKAKVQPYLDDFQKKWQEE |
| AI87-105 | SKDLEEVKAKVQPYLDDFQ |
| AI95-105 | AKVQPYLDDFQ |

Preferably, an Apo AI polypeptide of this invention is further characterized by its ability to immunologically mimic an epitope (antigenic determinant) expressed by Apo AI on substantially all HDL.

As used herein, the phrase "immunologically mimic" in its various grammatical forms refers to the ability of an Apo AI polypeptide of this invention to immunoreact with antibodies that recognize a conserved native epitope of Apo AI.

An Apo AI polypeptide of the present invention also referred to herein as a subject polypeptide, can be synthesized by any of the techniques that are known to those skilled in the polypeptide art, including recombinant DNA techniques. Synthetic chemistry techniques, such as a solid-phase Merrifield-type synthesis, are preferred for reasons of purity, antigenic specificity, freedom from undesired side products, ease of production and the like. An excellent summary of the many techniques available can be found in J. M. Steward and J. D. Young, "Solid Phase Peptide Synthesis", W. H. Freeman Co., San Francisco, 1969; M. Bodanszky, et al., "Peptide Synthesis", John Wiley & Sons, Second Edition, 1976 and J. Meienhofer, "Hormonal Proteins and Peptides", Vol. 2, p. 46, Academic Press (New York), 1983 for solid phase peptide synthesis, and E. Schroder and K. Kubke, "The Peptides", Vol. 1, Academic Press (New York), 1965 for classical solution synthesis, each of which is incorporated herein by reference. Appropriate protective groups usable in such synthesis are described in the above texts and in J. F. W. McOmie, "Protective Groups in Organic Chemistry", Plenum Press, New York, 1973, which is incorporated herein by reference.

In general, the solid-phase synthesis methods contemplated comprise the sequential addition of one or more amino acid residues or suitably protected amino acid residues to a growing peptide chain. Normally, either the amino or carboxyl group of the first amino acid residue is protected by a suitable, selectively removable protecting group. A different, selectively removable protecting group is utilized for amino acids containing a reactive side group such as lysine.

Using a solid phase synthesis as exemplary, the protected or derivatized amino acid is attached to an inert solid support through its unprotected carboxyl or amino group. The protecting group of the amino or carboxyl group is then selectively removed and the next amino acid in the sequence having the complimentary (amino or carboxyl) group suitably protected is admixed and reacted under conditions suitable for forming the amide linkage with the residue already attached to the solid support. The protecting group of the amino or carboxyl group is then removed from this newly added amino acid residue, and the next amino acid (suitably protected) is then added, and so forth. After all the desired amino acids have been linked in the proper sequence, any remaining terminal and side group protecting groups (and solid support) are removed sequentially or concurrently, to afford the final polypeptide.

It should be understood that a subject polypeptide need not be identical to the amino acid residue sequence of Apo AI, so long as it includes the required sequence and is able to immunoreact with antibodies that immunoreact with a conserved native epitope of Apo AI. Thus, substitutions of one amino acid for another, either conservative or non-conservative, where such changes provide for certain advantages in their use are contemplated. Conservative substitutions are those where one amino acid residue is replaced by another, biologically similar residue. Examples of conservative substitutions include the substitution of one hydrophobic residue such as isoleucine, valine, leucine or methionine for another, or the substitution of one polar residue for another such as between arginine and lysine, between glutamic and aspartic acids or between glutamine and asparagine and the like. The term "conservative substitution" also includes the use of a substituted amino acid in place of an unsubstituted parent amino acid provided that such a polypeptide also displays the requisite binding activity.

When a polypeptide of the present invention has a sequence that is not identical to the sequence of a Apo AI because one or more conservative or non-conservative substitutions have been made, usually no more than about 30 number percent, more usually no more than 20 number percent, and preferably no more than 10 number percent of the amino acid residues are substituted, except that the proline residue at position 99 cannot be substituted or deleted where additional residues have been added at either terminus for the purpose of providing a "linker" by which the polypeptides of this invention can be conveniently affixed to a label or solid matrix, or carrier, the linker residues do not form Apo AI epitopes, i.e., are not similar is structure to the Apo AI. Labels, solid matrices and carriers that can be used with the polypeptides of this invention are described hereinbelow.

Amino acid residue linkers are usually at least one residue and can be 40 or more residues, more often 1 to 10 residues, but do not form Apo AI epitopes. Typical amino acid residues used for linking are tyrosine, cysteine, lysine, glutamic and aspartic acid, or the like. In addition, a subject polypeptide can differ, unless otherwise specified, from the natural sequence of Apo AI by the sequence being modified by terminal-$NH_2$ acylation, e.g., acetylation, or thioglycolic acid amidation, by terminal-carboxlyamidation, e.g., with ammonia, methylamine, and the like.

When coupled to a carrier to form what is known in the art as a carrier-hapten conjugate, an Apo AI polypeptide of the present invention is capable of inducing antibodies that immunoreact with Apo AI, preferably Apo AI when it is part of an HDL particle (Apo AI/HDL). In view of the well established principle of immunologic cross-reactivity, the present invention therefore contemplates antigenically related variants of the polypeptides shown in Table 1. An "antigenically related variant" is a subject polypeptide that contains at least about 9 and no more than about 20 amino acid residues, includes the amino acid residue sequence AKVQPYLLD and is capable of inducing antibody molecules that immunoreact with a polypeptide from Table 1 and Apo AI.

C. Antibodies and Monoclonal Antibodies

The term "antibody" in its various grammatical forms is used herein as a collective noun that refers to a population of immunoglobulin molecules and/or immunologically active portions of immunoglobulin molecules, i.e., molecules that contain an antibody combining site or paratope.

An "antibody combining site" is that structural portion of an antibody molecule comprised of heavy and light chain variable and hypervariable regions that specifically binds antigen.

The phrase "antibody molecule" in its various grammatical forms as used herein contemplates both an intact immunoglobulin molecule and an immunologically active portion of an immunoglobulin molecule.

Exemplary antibody molecules are intact immunoglobulin molecules, substantially intact immunoglobulin molecules and those portions of an immunoglobulin molecule that contain the paratope, including those portions known in the art as Fab, Fab', F(ab')$_2$ and F(v).

Fab and F(ab')$_2$ portions of antibodies are prepared by the proteolytic reaction of papain and pepsin, respectively, on substantially intact antibodies by methods that are well known. See for example, U.S. Pat. No. 4,342,566 to Theofilopolous and Dixon. Fab' antibody portions are also well known and are produced from F(ab')$_2$ portions followed by reduction of the disulfide bonds linking the two heavy chain portions as with mercaptoethanol, and followed by alkylation of the resulting protein mercaptan with a reagent such as iodoacetamide. An antibody containing intact antibody molecules are preferred, and are utilized as illustrative herein.

A polyclonal antibody of the present invention is characterized as being capable of immunoreacting with 1) a subject polypeptide containing no more than 25 amino acid residue, and 2) Apo AI/HDL. A polyclonal antibody of the present invention is further characterized as being substantially free of antibody molecules that immunoreact with Apo AI CNBr1, CNBr3 and CNBr4.

The phrase "monoclonal antibody" in its various grammatical forms refers to a population of antibody molecules that contain only one species of antibody combining site capable of immunoreacting with a particular epitope. A monoclonal antibody thus typically displays a single binding affinity for any epitope with which it immunoreacts. A monoclonal antibody may therefore contain an antibody molecule having a plurality of antibody combining sites, each immunospecific for a different epitope, e.g., a bispecific monoclonal antibody.

A monoclonal antibody of the present invention is characterized as immunoreacting with:
 (a) Apo AI/HDL,
 (b) isolated Apo AI,
 (c) deamidated Apo AI/HDL,
 (d) Apo AI CNBr2, and
 (e) polypeptide AI90-105,
but as not immunoreacting with:
 (f) Apo AI CNBr1,
 (g) Apo AI CNBr3,
 (h) Apo AI CNBr4,
 (i) polypeptide AI90-105 (-P), and (j) polypeptide AI90-105 (G/P), and preferably is further characterized as not immunoreacting with:

(k) polypeptide AI93-101, and (l) polypeptide AI105-116.

A preferred monoclonal antibody of the present invention (subject monoclonal antibody) immunoreacts with a conserved native Apo AI/HDL epitope, and thus displays a ratio of immunoreactivities for Apo AI/HDL and deamidated Apo AI/HDL in the range of about 1:5 to about 5:1, preferably about 1:2.5 to about 2.5:1, and more preferably about 1.5:1 to about 1:1.5.

As used herein, the term "immunoreactivity" in its various grammatical forms refers to the concentration of antigen required to achieve a 50% inhibition of the immunoreaction between a given amount of the antibody and a given amount of Apo AI/HDL. That is, immunoreactivity is the concentration of antigen required to achieve a $B/B_o$ value of 0.5, where $B_o$ is the maximum amount of antibody bound in the absence of competing antigen and B is the amount of antibody bound in the presence of competing antigen, and both Bo and B have been adjusted for background. See, Rodbard, Clin. Chem., 20:1255–1270 (1974).

More preferably, a monoclonal antibody of the present invention has identical (indistinguishable) affinities for native Apo AI/HDL and deamidated Apo AI/HDL. That is a preferred monoclonal antibody has an affinity for Apo AI/HDL and an affinity for deamidated Apo AI/HDL that, when separately determined, are indistinguishable (equivalent) by statistical analysis to within a confidence limit of $p<0.1$, preferably $p<0.05$, more preferably $p<0.01$.

Methods for determining the affinity of a monoclonal antibody for an antigen and comparing those affinities for equivalence are well known in the art. See, for example, Muller, J. Immunol. Meth., 34:345–352 (1980) and Sokal et al., Biometry, W. H. Freeman & Co., (1981). A preferred method for determining monoclonal antibody affinity is by equilibrium competitive inhibition analysis. In that method, the ability of Apo AI/HDL and deamidated Apo AI to compete with Apo AI/HDL for binding to the monoclonal antibody being characterized are separately determined and compared for equivalence. See Tsao et al., J. Biol. Chem., 257:15222–15228 (1982).

For example, determining whether or not the affinities displayed by a monoclonal antibody for Apo AI/HDL and deamidated Apo AI/HDL are identical (indistinguishable) can be performed in the following manner:

(a) The percent of a known amount of the monoclonal antibody bound to solid-phase Apo AI/HDL in the presence of deamidated Apo AI/HDL present as liquid-phase competitor is determined at various known competitor concentrations. The logit transformation of each percent bound determination is then plotted against competitor (liquid-phase polypeptide) concentration. [Logit $(Y) = \log_e(Y/1-Y)$ where Y is the percent binding of monoclonal antibody in the presence of a given amount of competitor.]

(b) Using the same amount of monoclonal antibody as in step (a), the percent of antibody bound to solid-phase Apo AI/HDL in the presence of Apo AI/HDL present as liquid-phase competitor is determined at the same concentrations as the competitor in step (a). The logit transformation of each percent bound is then plotted against competitor (liquid-phase Apo AI/HDL) concentration.

(c) Linear regression analysis is preformed on each of the plots obtained in steps (a) and (b) to obtain their respective slopes.

(d) The slopes obtained for Apo AI/HDL and the slope obtained for deamidated Apo AI/HDL are then compared using a test for equality of slopes, such as that described by Sokal et al., supra, p.485, Box 14.5.

In preferred embodiments, a subject monoclonal antibody displays a ratio of immunoreactivities for Apo AI/HDL and a subject polypeptide, preferably a polypeptide shown in Table 1 and more preferably AI90-105, in the range of about 1:5 to about 5:1, preferably about 1:25 to about 2.5:1, and more preferably about 1.5:1 to about 1:1.5, when the immunoreactivities are determined using molar equivalents of Apo AI and peptide.

Further preferred is a monoclonal antibody that has identical affinities for Apo AI/HDL and a subject polypeptide, preferably a polypeptide shown in Table 1 and more preferably AI90-105. Screening for identical affinities is accomplished as previously described using molar equivalents of peptide and Apo AI in steps (a) and (b).

A subject monoclonal antibody, typically containing whole antibody molecules can be prepared using the polypeptide-induced hybridoma technology described by Niman et al., Proc. Natl. Sci., U.S.A., 80:4949–4953 (1983), which description is incorporated herein by reference. Briefly, to form the hybridoma from which the monoclonal antibody composition is produced, a myeloma or other self-perpetuating cell line is fused with lymphocytes obtained from the spleen of a mammal hyperimmunized with a polypeptide of this invention.

It is preferred that the myeloma cell line be from the same species as the lymphocytes. Typically, a mouse of the strain 129 G1X+ is the preferred mammal. Suitable mouse myelomas for use in the present invention include the hypoxanthine-aminopterin-thymidine-sensitive (HAT) cell lines P3X63-Ag8.653, and Sp2/0-Ag14 that are available from the American Type Culture Collection, Rockville, Md., under the designations CRL 1580 and CRL 1581, respectively.

Splenocytes are typically fused with myeloma cells using polyethylene glycol (PEG) 1500. Fused hybrids are selected by their sensitivity to HAT. Hybridomas producing a monoclonal antibody of this invention are identified using the radioimmunoassay (RIA) and the enzyme linked immunosorbent assay (ELISA) described in Examples 6 and 7, respectively.

A monoclonal antibody of the present invention can be produced by initiating a monoclonal hybridoma culture comprising a nutrient medium containing a hybridoma that secretes antibody molecules of the appropriate polypeptide specificity. The culture is maintained under conditions and for a time period sufficient for the hybridoma to secrete the antibody molecules into the medium. The antibody-containing medium is then collected. The antibody molecules can then be further isolated by well known techniques.

Media useful for the preparation of these compositions are both well known in the art and commercially available and include synthetic culture media, inbred mice and the like. An exemplary synthetic medium is Dulbecco's minimal essential medium (DMEM; Dulbecco et al., *Virol.* 8:396 (1959)) supplemented with 4.5 gm/l glucose, 20 mm glutamine, and 20% fetal calf serum. An exemplary inbred mouse strain is the Balb/c.

The monoclonal antibody produced by the above method can be used, for example, in diagnostic and therapeutic modalities wherein formation of an Apo AI-containing immunoreaction product is desired.

A hybridoma useful in producing a subject monoclonal antibody, i.e., MAB AI-18, is hybridoma HI3505, said hybridoma being deposited pursuant to Budapest Treaty Requirements with the American Type Culture Collection (ATCC), Rockville, Md. 20852 U.S.A. on 14 Oct. 1987 and given the ATCC designation HB9570. It should be noted that hybridoma ATCC HB9570 can be used, as is well known in the art, to produce other immortal cell lines that produce a subject monoclonal antibody, and thus production of a subject monoclonal antibody is not dependent on culturing hybridoma by ATCC HB9570 per se.

D. Diagnostic Systems

A diagnostic system in kit form of the present invention includes, in an amount sufficient for at least one assay, a subject Apo AI polypeptide and/or a subject monoclonal antibody, as separately packaged immunochemical reagents. Instructions for use of a packaged immunochemical reagent are also typically included.

As used herein, the term "package" refers to a solid matrix or material such as glass, plastic, paper, foil and the like capable of holding within fixed limits a polypeptide, polyclonal antibody or monoclonal antibody of the present invention. Thus, for example, a package can be a glass vial used to contain milligram quantities of a contemplated polypeptide or it can be a microtiter plate well to which microgram quantities of a contemplated polypeptide have been operatively affixed, i.e., linked so as to be capable of being immunologically bound by an antibody.

"Instructions for use" typically include a tangible expression describing the reagent concentration or at least one assay method parameter such as the relative amounts of reagent and sample to be admixed, maintenance time periods for reagent/sample admixtures, temperature, buffer conditions and the like.

In preferred embodiments, a diagnostic system of the present invention further includes a label or indicating means capable of signaling the formation of a complex containing a polypeptide or antibody molecule of the present invention.

The word "complex" as used herein refers to the product of a specific binding reaction such as an antibody-antigen or receptor-ligand reaction. Exemplary complexes are immunoreaction products.

As used herein, the terms "label" and "indicating means" in their various grammatical forms refer to single atoms and molecules that are either directly or indirectly involved in the production of a detectable signal to indicate the presence of a complex. Any label or indicating means can be linked to or incorporated in an expressed protein, polypeptide, or antibody molecule that is part of an antibody or monoclonal antibody composition of the present invention, or used separately, and those atoms or molecules can be used alone or in conjunction with additional reagents. Such labels are themselves well-known in clinical diagnostic chemistry and constitute a part of this invention only insofar as they are utilized with otherwise novel proteins methods and/or systems.

The labeling means can be a fluorescent labeling agent that chemically binds to antibodies or antigens without denaturing them to form a fluorochrome (dye) that is a useful immunofluorescent tracer. Suitable fluorescent labeling agents are fluorochromes such as fluorescein isocyanate (FIC), fluorescein isothiocyante (FITC), 5-dimethylamine-1-naphthalenesulfonyl chloride (DANSC), tetramethylrhodamine isothiocyanate (TRITC), lissamine, rhodamine 8200 sulphonyl chloride (RB 200 SC) and the like. A description of immunofluorescence analysis techniques is found in DeLuca, "Immunofluorescence Analysis", in *Antibody As a Tool*, Marchalonis, et al., eds., John Wiley & Sons, Ltd., pp. 189–231 (1982), which is incorporated herein by reference.

In preferred embodiments, the indicating group is an enzyme, such as horseradish peroxidase (HRP), glucose oxidase, or the like. In such cases where the principal indicating group is an enzyme such as HRP or glucose oxidase, additional reagents are required to visualize the fact that a receptor-ligand complex (immunoreactant) has formed. Such additional reagents for HRP include hydrogen peroxide and an oxidation dye precursor such as diaminobenzidine. An additional reagent useful with glucose oxidase is 2,2'-azino-di-(3-ethyl-benzthiazoline-G-sulfonic acid) (ABTS).

Radioactive elements are also useful labeling agents and are used illustratively herein. An exemplary radiolabeling agent is a radioactive element that produces gamma ray emissions. Elements which themselves emit gamma rays, such as $^{124}$I, $^{125}$I, $^{128}$I, $^{132}$I and $^{51}$Cr represent one class of gamma ray emission-producing radioactive element indicating groups. Particularly preferred is $^{125}$I. Another group of useful labeling means are those elements such as $^{11}$C, $^{18}$F, $^{15}$O and $^{13}$N which themselves emit positrons. The positrons so emitted produce gamma rays upon encounters with electrons present in the animal's body. Also useful is a beta emitter, such $^{111}$indium of $^3$H.

The linking of labels, i.e., labeling of, polypeptides and proteins is well known in the art. For instance, antibody molecules produced by a hybridoma can be labeled by metabolic incorporation of radioisotope-containing amino acids provided as a component in the culture medium. See, for example, Galfre et al., *Meth. Enzymol.*, 73:3–46 (1981). The techniques of protein conjugation or coupling through activated functional groups are particularly applicable. See, for example, Aurameas, et al., *Scand J. Immunol.*, Vol. 8 Suppl. 7:7–23 (1978), Rodwell et al., *Biotech.*, 3:889–894 (1984), and U.S. Pat. No. 4,493,795.

The diagnostic systems can also include, preferably as a separate package, a specific binding agent. A "specific binding agent" is a molecular entity capable of selectively binding a reagent species of the present invention or a complex containing such a species, but is not itself a polypeptide or antibody molecule composition of the present invention. Exemplary specific binding agents are second antibody molecules, complement proteins or fragments thereof, *S. aureus* protein A, and the like. Preferably the specific binding agent binds the reagent species when that species is present as part of a complex.

In preferred embodiments, the specific binding agent is labeled. However, when the diagnostic system includes a specific binding agent that is not labeled, the agent is typically used as an amplifying means or reagent. In these embodiments, the labeled specific binding agent is capable of specifically binding the amplifying means when the amplifying means is bound to a reagent species-containing complex.

The diagnostic kits of the present invention can be used in an "ELISA" format to detect the quantity of Apo AI in a vascular fluid sample such as blood, serum, or plasma. "ELISA" refers to an enzyme-linked immunosorbent assay that employs an antibody or antigen bound to a solid phase and an enzyme-antigen or enzyme-antibody conjugate to detect and quantify the amount of an antigen present in a sample. A description of the ELISA technique is found in Chapter 22 of the 4th Edition of *Basic and Clinical Immunology* by D. P. Sites et al., published by Lange Medical Publications of Los Altos, Calif. in 1982 and in U.S. Pat. Nos. 3,654,090; 3,850,752; and 4,016,043, which are all incorporated herein by reference.

Thus, in preferred embodiments, an Apo AI polypeptide, or monoclonal antibody of the present invention can be affixed to a solid matrix to form a solid support that comprises a package in the subject diagnostic systems.

A reagent is typically affixed to a solid matrix by adsorption from an aqueous medium although other modes of affixation applicable to proteins and polypeptides well known to those skilled in the art, can be used.

Useful solid matrices are also well known in the art. Such materials are water insoluble and include the cross-linked dextran available under the trademark SEPHADEX from Pharmacia Fine Chemicals (Piscataway, N.J.); agarose; beads of polystyrene beads about 1 micron to about 5 millimeters in diameter available from Abbott Laboratories of North Chicago, Ill.; polyvinyl chloride, polystyrene, cross-linked polyacrylamide, nitrocellulose- or nylon-based webs such as sheets, strips or paddles; or tubes, plates or the wells of a microtiter plate such as those made from polystyrene or polyvinylchloride.

The reagent species, labeled specific binding agent or amplifying reagent of any diagnostic system described herein can be provided in solution, as a liquid dispersion or as a substantially dry power, e.g., in lyophilized form. Where the indicating means is an enzyme, the enzyme's substrate can also be provided in a separate package of a system. A solid support such as the before-described microtiter plate and one or more buffers can also be included as separately packaged elements in this diagnostic assay system.

The packaging materials discussed herein in relation to diagnostic systems are those customarily utilized in diagnostic systems. Such materials include glass and plastic (e.g., polyethylene, polypropylene and polycarbonate) bottles, vials, plastic and plastic-foil laminated envelopes and the like.

E. Assay Methods

The present invention contemplates various immunoassay methods for determining the amount of Apo AI in a biological fluid sample using a polypeptide, polyclonal antibody or monoclonal antibody of this invention as an immunochemical reagent to form an immunoreaction product whose amount relates, either directly or indirectly, to the amount of Apo AI in the sample. Those skilled in the art will understand that there are numerous well known clinical diagnostic chemistry procedures in which an immunochemical reagent of this invention can be used to form an immunoreaction product whose amount relates to the amount of Apo AI present in a body sample. Thus, while exemplary assay methods are described herein, the invention is not so limited.

Various heterogenous and homogeneous protocols, either competitive or noncompetitive, can be employed in performing an assay method of this invention. For example, the present invention contemplates a competitive method for assaying the amount of Apo AI in a vascular fluid sample which comprises the steps of:

(a) Forming an immunoreaction admixture by admixing a vascular fluid sample with:
  (i) a monoclonal antibody of the present invention, preferably AI-18, and
  (ii) an Apo AI polypeptide of the present invention, preferably AI90-105.

Preferably, the vascular fluid sample is provided as a known amount of blood, or a blood derived product such as serum or plasma. Regardless of the type of sample used, it is preferably obtained from a person who has fasted at least about 12 hours as is known in the art. Such a sample is referred to as a "fasting" sample. It is also noted that where serum or plasma is used as the sample, that sample need not be subjected treatment with a denaturing or chaotropic agent for purposes of altering the expression of the Apo AI epitope being assayed.

Preferably, the amount of monoclonal antibody that is admixed is known. Further preferred are embodiments where the monoclonal antibody is labeled, i.e., operatively linked to an indicating means such as an enzyme, radionuclide and the like.

Preferably, the Apo AI polypeptide is present as part of a solid support, i.e., operatively linked to a solid matrix, so that the immunoreaction admixture formed has a solid and a liquid phase. Further preferred are embodiments wherein the amount of polypeptide present in the immunoreaction admixture is an amount sufficient to form an excess of epitopes relative to the number of antibody combining sites present in the immunoreaction admixture capable of immunoreacting with those epitopes.

(b) The immunoreaction admixture is maintained under biological assay conditions for a predetermined time period such as about 10 minutes to about 16–20 hours at a temperature of about 4 degrees C. to about 45 degrees C. that, such time being sufficient for the Apo AI present in the sample to immunoreact with (immunologically bind) a portion of the anti-Apo AI antibody combining sites present in the monoclonal antibody to form an Apo AI-containing immunoreaction product.

Biological assay conditions are those that maintain the biological activity of the immunochemical reagents of this invention and the Apo AI sought to be assayed. Those conditions include a temperature range of about 4 degrees C. to about 45 degrees C., a pH value range of about 5 to about 9 and an ionic strength varying from that of distilled water to that of about one molar sodium chloride. Methods for optimizing such conditions are well known in the art.

(c) The amount of Apo AI-containing immunoreaction product that formed is determined, and thereby the amount of Apo AI in the sample.

Determining the amount of the Apo AI-containing immunoreaction product, either directly or indirectly, can be accomplished by assay techniques well known in the art, and typically depend on the type of indicating means used.

In preferred competitive assay methods, the amount of product determined in step (c) is related to the amount of immunoreaction product similarly formed and determined using a control sample in place of the vascular fluid sample, wherein the control sample contains a known amount of a subject polypeptide, preferably AI90-105.

In another embodiment, the present invention contemplates a double antibody or "sandwich" immunoassay comprising the steps of:

(a) Forming a first immunoreaction admixture by admixing a vascular fluid sample with a first antibody, preferably a monoclonal antibody, wherein the antibody and Apo AI/HDL present in the sample are capable of forming a first immunoreaction product that can immunoreact with a subject monoclonal antibody, preferably MAB AI-18. Preferably the first antibody is operatively linked to a solid matrix.

(b) Maintaining the first immunoreaction admixture so formed under biological assay conditions for a time period sufficient to form the first immunoreaction product. Preferably, the first immunoreaction product is then separated from the sample.

(c) Forming a second immunoreaction admixture by admixing the first immunoreaction product with:
  (i) a monoclonal antibody of the present invention, preferably MAB AI-18, and
  (ii) an Apo AI polypeptide of the present invention, preferably AI90-105. Preferably, step (ii) is performed prior to step (i) or substantially simultaneously therewith, i.e., within about 5-10 minutes, preferably within about 1-2 minutes.

(d) Maintaining the second immunoreaction admixture so formed under biological assay conditions for a true period sufficient to form the second or "sandwich" immunoreaction product.

(e) Determining the amount of second immunoreaction product that formed, and thereby the amount of Apo AI in the sample.

Preferably, the subject monoclonal antibody of step (c)(i) is labeled, preferably with an enzyme, and the second immunoreaction product formed is a labeled product.

In preferred double antibody assay methods, the amount of immunoreaction product determined in step (e) of the double antibody method is related to the amount of immunoreaction product similarly formed and determined using a control sample in place of the vascular fluid sample, wherein the control sample contains a known amount of a subject polypeptide, preferably AI90-105.

EXAMPLES

The following Examples illustrate, but do not limit, the present invention.

1. Preparation of Antigens

A. Polypeptides

Polypeptides AI90-105, AI87-105, AI87101, AI90-111, AI101-111, AI93-101, AI95-105 and AI96-101 were synthesized using the classical solid-phase technique described by Merrifield, *Adv. Enzymol.*, 32:221-96 (1969) as adapted for use with a Model 430A automated peptide synthesizer (Applied Biosystems, Foster City, Calif.). Polypeptide resins were cleaved by hydrogen fluoride, extracted and analyzed for purity by high-performance liquid chromatograph using a reverse-phase C18 column. (Waters Associates, Mildord, Mass.).

The amino acid residue sequences of polypeptides AI90-105, AI87-105, AI95-105 and AI90-101 were previously shown in Table 1. The sequences of polypeptides AI101-111, AI87-101, AI93-101, AI95-105(-P) and AI95-105(G/P) are shown in Table 2 below.

TABLE 2

| Peptide Designation | Amino Acid Residue Sequence[a] |
|---|---|
| AI90-111 | LEEVKAKVQPYLDDFQKKWQEE |
| AI101-111 | LDDFQKKWQEE |
| AI87-101 | SKDLEEVKAKVQPYL |
| AI93-101 | VKAKVQPYL |
| AI95-105(-P)[1] | AKVQYLDDFQ |
| AI95-105(G/P)[2] | AKVQGYLDDFQ |
| AI100-105 | YLDDFQ |
| AI105-116 | QKKWQEEMELYR |
| AI96-101 | KVQPYL |

[1]A polypeptide whose amino acid residue sequence corresponds to the sequence of Apo AI from positions 95 through 105 except that the proline at position 99 has been deleted.
[2]A polypeptide whose amino acid residue sequence corresponds to the sequence of Apo AI from positions 95 through 105 except that glycine has been substituted for proline at position 99.

B. Preparation of Apo AI/HDL

HDL was isolated from plasma obtained by plasmaphoresis of normal fasting-donor blood at the local blood bank (San Diego Plasma Center, San Diego, Calif.). For that purpose, plasma so obtained was adjusted to contain a final concentration of 5 millimolar (mM) benzamidine, 1 mM diisopropyl fluorophosphate, 10 mM ethylenediaminetetraacetic acid (EDTA), 10 milligrams per milliliter (mg/ml) soybean trypsin inhibitor and 10,000 units per ml aprotinin. The HDL was then isolated from this adjusted plasma by sequential ultracentrifugation using solid potassium bromide (KBr) for density adjustment.

First, the adjusted plasma was centrifuged at about 2000,000×g for 18 to 24 hours and the bottom layer of the resulting supernatant was recovered. Solid KBr was admixed to the bottom layer until the density was greater than 1.063 grams per milliliter (g/ml). The resulting admixture was then layered under a 0.1% EDTA solution containing KBr at density of 1.063 g/ml and centrifuged at 200,000×g for more than 48 hours. The bottom layer was again recovered and to it was admixed solid KBr until the density was adjusted to greater than 1.21 g/ml. That adjusted layer was layered under a 0.1% EDTA solution containing KBr at a density of 1.21 g/ml, and was centrifuged at 200,000×g for more than 48 hours.

The top layer was then recovered and solid KBr was admixed until the density was greater than 1.063 g/ml. That adjusted top layer was layered under a 0.1% EDTA solution containing KBr at a density of 1.063 g/ml, and still further centrifuged at 200,000×g for more than 48 hours.

The middle layer was recovered and solid KBr was admixed to it until the density was adjusted to greater than 1.21 g/ml. That adjusted middle layer was layered under a 0.1% EDTA solution containing KBr at a density of 1.21 g/ml and centrifuged at 300,000×g for more than 48 hours. The resulting HDL-containing top layer, having a density equal to 1.063 to 1.21 g/ml, was recovered. The recovered HDL was dialyzed against lipoprotein buffer (LLB; water containing 150 mM NaCl, 1 mM EDTA, 0.005% alpha-tecopherol, and 5 mM benzamidine) and the resulting Apo AI/HDL was stored under sterile conditions for no more than 21 days.

C. Preparation of Delipidated Apo AI

Delipidated Apo AI was prepared by organically extracting the lipids from Apo AI/HDL. A sample of the Apo AI/HDL prepared in Example 1B was first dialyzed against 0.01 percent EDTA having a pH value of 7.5 overnight (approximately 18 hours), then dialyzed against 0.003 percent EDTA for approximately 12 hours, and subsequently lyophilized at 10 to 20 milligrams of protein per tube. To each tube were admixed 35 ml of absolute ethanol:anhydrous ether (1:1) at 4 degrees C. Following mixture, the solution was maintained for 20 minutes at −20 degrees C. The solution was then centrifuged for 30 minutes at $1000 \times g$ at zero degrees C., the supernatant was poured off and the Apo AI-containing pellet was retained.

The ethanol ether extraction as described above was performed twice again for a total of three extractions. Subsequently, 35 ml of anhydrous ether at 4 degrees C. were admixed to the sample. The admixture was maintained for 30 minutes at −20 degrees C., spun at $1000 \times g$ for 30 minutes at −20 degrees C., and the Apo AI-containing pellet was recovered and dried using nitrogen gas to form delipidated Apo AI. It should be noted that delipidated Apo AI contains not only Apo AI, but also other proteins associated with the HDL, such as Apo AI.

D. Preparation of Isolated Apo AI

Apo AI was isolated from delipidated Apo AI by size fractionation using high pressure liquid chromatography (HPLC) following the procedures of Kinoshita et al., *J. Biochem.*, 94:615–617 (1983). About 300 mg of delipidated Apo AI was dissolved in 200 microliters (ul) of 0.1% sodium dodecyl sulfate (SDS), 0.1M sodium phosphate (pH 7.0) and size fractionated on Spherogel—TSK 3000 SW HPLC columns (Beckman Instruments Inc., Fullerton, Calif.). Fractions containing the isolated Apo AI were stored at minus 20 degrees C. Apo AI was also isolated by delipidation and electrophoresis on polyacrylamide as described herein.

E. Preparation of Polyacrylamide-HDL

HDL was immobilized in polyacrylamide by admixing the following designated amounts of separately prepared solutions to form a cross-linking reaction admixture:

(a) 4.3 ml of LLB containing 50 mg HDL,
(b) 1.25 ml water containing 28% (w/v) acrylamide
(c) 2.5 ml water containing 2% (w/v) N,N'methylene-bis arcylamide
(d) 1.25 ml of LLB
(e) 1.2 ml water containing 1% (w/v) ammonium persulfate.

The cross-linking reaction was allowed to proceed for about 16 hours at 37° C. Because cross-linking did not occur, TEMED (N,N,N',N'-tetramethylethylemediamine) was subsequently admixed producing cross-linking within about 90 minutes at 37° C. The resulting polyacrylamide mass was mechanically homogenized in the presence of 20 ml LLB and then washed with LLB by centrifugation filtration to form polyacrylmide-HDL

2. Generation of Monoclonal Antibodies

Balb/c ByJ mice (Scripps Clinic and Research Foundation Vivarium, La Jolla, Calif.) were immunized intraperitoneally (i.p.) with 50 ug of polyacrylamide-HDL as immunogen in complete Freund's adjuvant (CFA) and 500 units of interferon-gamma followed by a second and third immunization, each about three weeks apart, in incomplete Freund's adjuvant (IFA) without interferon. About nine months after the last adjuvant-containing immunization, the mice received a boost of 50 ug of native HDL intravenously (i.v.) in normal saline 4 days prior to fusion and a second similar perfusion boost one day later.

The animals so treated were sacrificed and the spleen of each mouse was harvested. A spleen cell suspension was then prepared. Spleen cells were then extracted from the spleen cell suspension by centrifugation for about 10 minutes at 1000 r.p.m., at 23 degrees C. Following removal of supernatant, the cell pellet was resuspended in 5 ml cold $NH_4Cl$ lysing buffer, and was incubated for about 10 minutes.

To the lysed cell suspension were admixed 10 ml Dulbecco's Modified Eagle Medium (DMEM) (GIBCO) and HEPES [4-(2-hydroxyethyl)-1-piperidineethanesulfonic acid] buffer, and that admixture was centrifuged for about 10 minutes at 1000 r.p.m., at 23 degrees C.

The supernatant was decanted, the pellet was resuspended in 15 ml of DMEM and HEPES, and was centrifuged for about 10 minutes at 1000 r.p.m. at 23 degrees C. The above procedure was repeated.

The pellet was then resuspended in 5 ml DMEM and HEPES. An aliquot of the spleen cell suspension was then removed for counting. Fusions were accomplished in the following manner using the nonsecreting mouse myeloma cell line P3X63Ag8.653.1, a subclone of line P3x63Ag 8.653 (ATCC 1580). Using a myeloma to spleen cell ratio of about 1 to 10 or about 1 to 5, a sufficient quantity of myeloma cells were centrifuged into a pellet, washed twice in 15 ml DMEM and HEPES, and centrifuged for 10 minutes at 1000 r.p.m. at 23 degrees C.

Spleen cells and myeloma cells were combined in round bottom 15 ml tubes. The cell mixture was centrifuged for 10 minutes at 1000 r.p.m. at 23 degrees C., and the supernatant was removed by aspiration. Thereafter, 200 ul of 50 percent (weight per volume) aqueous polyethylene glycol 4000 molecular weight (PEG; ATCC Baltimore, Md.) at about 37 degrees C. were admixed using a 1 ml pipette with vigorous stirring to disrupt the pellet, and the cells were gently mixed for between 15 and 30 seconds. The cell mixture was centrifuged 4 minutes at 700 r.p.m.

At about 8 minutes from the time of adding the PEG, 5 ml of DMEM plus HEPES buffer were admixed slowly to the pellet, without disturbing the cells. After 1 minute, the resulting admixture was broken up with a 1 ml pipette, and was incubated for an additional 4 minutes. This mixture was centrifuged for 7 minutes at 1000 r.p.m. The supernatant was decanted, 5 ml of HT (hypoxanthine/thymidine) medium were slowly admixed to the pellet, and the admixture was maintained undisturbed for 5 minutes. The pellet was then broken into large chunks, and the final cell suspension was placed into T75 flasks (2.5 ml per flask) into which 7.5 ml HT medium had been placed previously. The resulting cell suspension was incubated at 37 degrees C. to grow the fused cells. After 245 hours, 10 ml of HT medium were admixed to the flasks, followed 6 hours later by admixture of 0.3 ml of 0.04 mM aminopterin. 48 hours after fusion, 10 ml of HAT (hypoxanthine/aminopterin/thymidine) medium were admixed to the flasks.

Three days after fusion, viable cells were plated out in 96-well tissue culture plates at about $2 \times 10^4$ viable cells per well (768 total wells) in HAT buffer medium as described in Kennett et al., Curr. Top. Microbiol. Immunol., 81:77 (1978). The cells were fed seven days after fusion with HAT medium and at approximately 4–5 day intervals thereafter as needed with HT medium. Growth was followed microscopically, and culture supernatants were collected about two weeks later and assayed for the presence of HDL-specific antibody by solid phase radioimmunoassay (RIA) essentially as described in Curtiss and Edgington J. Biol. Chem., 257:15213–15221 (1982).

Briefly, 50 ul of PBS containing 5 ug/ml Apo AI/HDL were admixed into the wells of microtiter plates. The plates were maintained overnight (about 16 hours) at 4 degrees C. to permit the Apo AI/HDL to adhere to well walls. After washing the wells four times with SPRIA buffer (2.68 mM KCl, 1.47 mM $KH_2PO_4$, 137 mM NaCl, 8.03 mM $Na_2HPO_4$, 0.05% Tween-20, 0.1 KIU/ml Traysol, 0.1% BSA, 0.015% $NaN_3$), 200 ul of SPRIA buffer containing 3% normal goat serum (NGS) and 3% bovine serum albumin (BSA) were admixed to each well to block excess protein binding sites. The plates were maintained for 30 minutes at 20 degrees C., the wells emptied by shaking, and blotted dry to form a solid-support, i.e., a solid matrix to which Apo AI/HDL was operatively affixed.

To each well was then admixed 50 ul of hybridoma tissue culture supernatant to form a solid-liquid phase immunoreaction admixture. The admixture was maintained for 2 hours at 37 degrees C. to permit formation of solid-phase immunoreaction products. After washing the wells as previously described, 50 ul of $^{125}$I-labeled goat anti-mouse IgG at 0.25 ug protein per ml were admixed to each well to form a labeling reaction admixture. That admixture was maintained for 1 hour at 37 degrees C. to permit formation of $^{125}$I-labeled solid-phase immunoreaction products. After washing the wells as previously described, the amount of $^{125}$I-labeled product bound to each well was determined by gamma scintillation.

Hybridoma AI-18 was selected from about 16 hybridoma cultures that secreted anti-HDL antibodies into their culture media, and further characterized as described herein.

3. Monoclonal Antibody Preparation Purification

Ascites fluids were obtained from 10 week old Balb/c mice, which had been primed with 0.3 ml of mineral oil and injected intraperitoneally with $5 \times 10^6$ hybridoma cells. The average time for development of ascites was 9 days. Following clarification by centrifugation at $15,000 \times g$ for 15 minutes at 23 degrees C., ascites fluids produced by hybridoma H135D3 were pooled and stored frozen at −20 degrees C.

Purified AI-18 monoclonal antibody each of the five hybridomas were prepared by fast protein liquid chromatography (FPLC) using a Pharmacia Mono Q HR5/5 anion exchange column (Pharmacia Fine Chemicals, Piscataway, N.J.) using a 0–0.5 molar (M) NaCl gradient in 10 mM Tris, pH 8.0 following directions supplied with the column. Purified Mabs were concentrated using an Amicon stirred ultrafiltration cell (Danvers, Mass.; PM 30 membrane) to a concentration of 1 mg/ml, dialyzed into PBS (phosphate-buffered saline, pH 7.2) and stored at −70 degrees C.

4. Radioiodination

Radioiodination of HDL, Apo AI and immunochemically purified goat anti-mouse Ig was performed enzymatically utilizing the Enzymobead iodination procedure and Enzymobeads obtained from Biorad, (Burlingame, Calif.). The Enzymobead iodination was utilized to characterize the antigens and antibodies for the solid phase radioimmunoassay as discussed below.

5. Apo AI-Cyanogen Bromide Fragment Specificity

The Apo AI CNBr fragment specificity of MAB AI-18 was determined by Western blot analysis according to the method in Curtiss et al., Proceeding of the Workshop on Lipoprotein Heterogeneity, Ed. by Lippel, NIH Publication No. 87-2646 p. 363–377 (1987). Briefly CNBr fragmentation was performed on isolated Apo AI dissolved in 90% formic acid. CNBr was added in a 13,000 molar excess and the reaction mixture was maintained about 15 hours at about 20 degrees C. Following lyophilization, the resulting CNBr fragments were solubilized in 1% SDS, 0.01M Tris, pH 8.2 and subjected to isoelectric focusing in 6% polyacrylamide slab gels containing 8M urea and 2% ampholine (pH 4 to pH 6) as described by Curtiss et al., J. Biol. Chem., 260:2982–93 (1985). Electrophoretically separated proteins were transferred to nitrocellulose for immunoreaction with MAB AI-18. Production of immunoreaction products was detected by radioiodimated goat anti-mouse Ig followed by autoradiography.

The results of these studies indicate that MAB AI-18 does not immunoreact with Apo AI CNBr fragments CNBr1, CNBr3 and CNBr4 but does immunoreact with CNBr2. It should also be noted that these results indicate that MAB AI-18 immunoreacts with isolated Apo AI.

6. MAB AI-18 Immunoreactivity

The immunoreactivity of MAB AI-18 for native Apo AI/HDL, deamidated Apo AI/HDL and various polypeptides was examined by a competitive RIA performed as follows:

One hundred ul of PBS (0.15M NaCl, 0.01M $NaPO_4$, pH 7.2) containing 10 ug/ml Apo AI/HDL were admixed to the wells of microtiter plates. The plates were maintained for 1 hour at 20 degrees C. on a rotating platform to allow the Apo AI/HDL to adhere to the wells and form solid supports. After aspirating excess liquid from the wells, 200 ul of block solution (3% BSA, 3% NGS in PBS) was admixed to each well, and the wells were maintained for 30 minutes at 20 degrees C. on a rotating platform. Subsequently, the blocking solution was removed by aspiration and the wells were washed 3 times with SPRIA buffer.

To each well was then admixed first 50 ul of PBS containing 3% BSA and various concentrations of competitor antigen, i.e., Apo AI/HDL, deamidated Apo AI/HDL or peptide, and second, 50 ul of MAB AI-18 in the form of clarified ascites diluted $1:1.25 \times 10^5$ in PBS containing 3% BSA to form competitive immunoreaction admixtures. In control wells either competing antigen or antibody was replaced by PBS containing 3% BSA.

The immunoreaction admixtures were maintained about 16 hours at 4 degrees C. on a rotating platform to permit formation of solid-phase immunoreaction products. After washing the wells as previously described, 100 ul of $^{125}$I-labeled goat anti-mouse Ig ($^{125}$I-goat anti-mouse Ig diluted to $2 \times 10^5$ trichloracetic acid precipitable disintegrations per minute per 100 ul in PBS containing 3% BSA) were admixed to each well. The labeling immunoreaction admixtures so formed were maintained for 4 hours at 4 degrees C. on a rotating platform. Subsequently, the wells were washed with SPRIA as previously described and the amount of $^{125}$I-labeled solid-phase immunoreaction product formed was determined.

Figure 2:
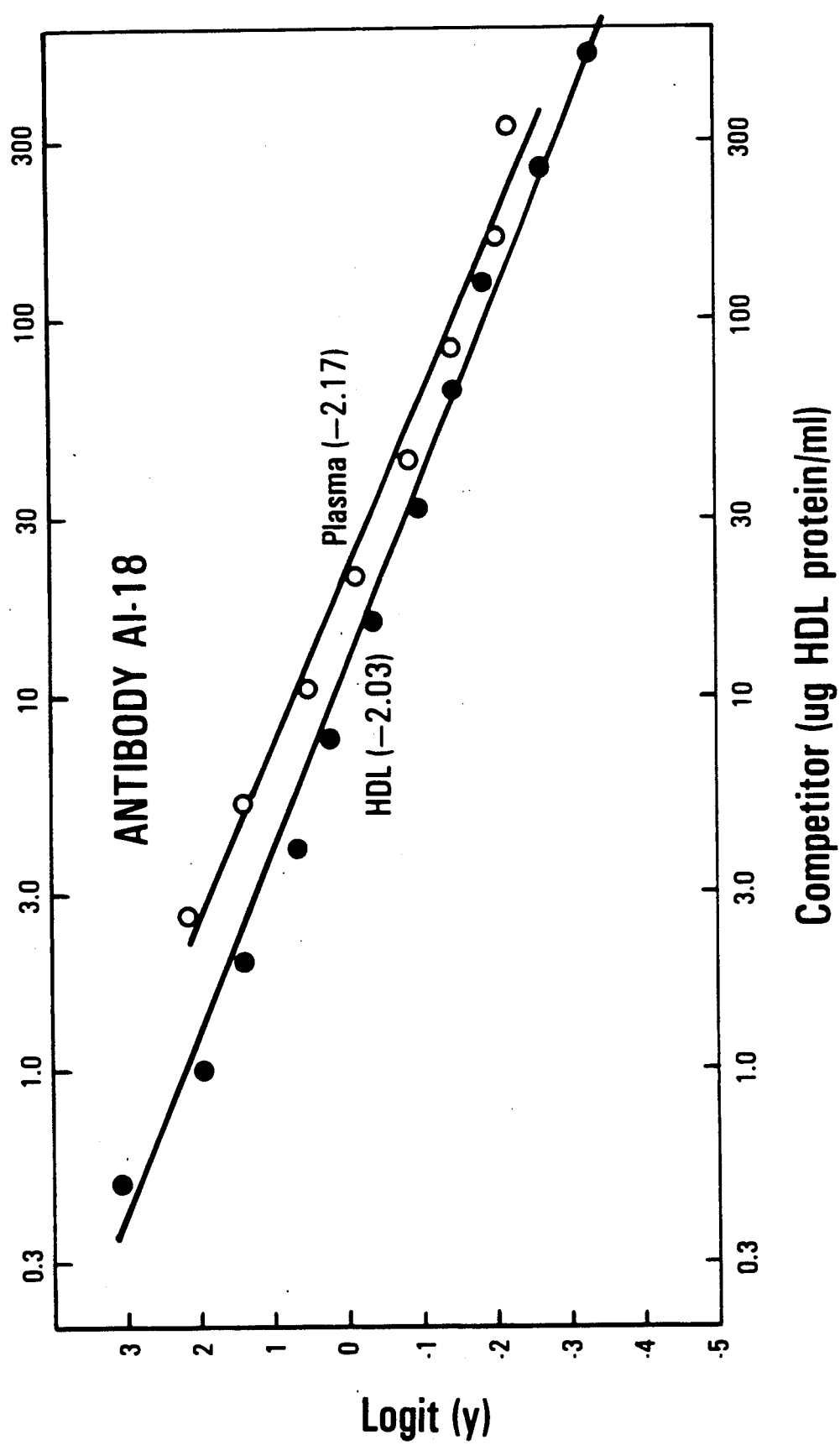
FIG. 2 illustrates the ability of Apo AI/HDL and HDL present in fresh plasma to competitively inhibit AI-18 to Apo AI/HDL. Protein concentration were determined according to the method of Markwell et al., *Anal. Biochem.*, 87:206-120 (1978). The logit transformed HD1 (●) and plasma (O) data displayed a slopes of −2.03 and −2.17, respectively.

The ability of MAB AI-18 to immunoreact with Apo AI/HDL and HDL in fresh plasma was compared by using each as a competitor in the above described RIA. The results of this study are shown in FIG. 2. The slopes of the HDL and plasma logit transformed data were found to be −2.03 and −2.17. While statistical analysis has not yet been performed, it is believed that the two slopes are equivalent.

In studies examining the immmunoreactivity of MAB AI-18 for deamidated Apo AI/HDL, Apo AI/HDL was subjected to deamidation using 7 different NaOH concentrations as described in Table 3 below:

TABLE 3

| Sample Designation | NaOH Treatment of Apo AI/HDL[1] | | | | |
|---|---|---|---|---|---|
| | Volumes Admixed[2] | | | | |
| | Apo AI[2] /HDL | 1N NaOH | 0.01N NaOH | H$_2$O | pH |
| A | 500 | 0 | 0 | 250 | 6.26 |
| B | 500 | 0 | 5 | 245 | 6.34 |
| C | 500 | 0 | 50 | 200 | 7.04 |
| D | 500 | 5 | 0 | 245 | 10.67 |
| E | 500 | 15 | 0 | 235 | 11.33 |
| F | 500 | 50 | 0 | 100 | 11.86 |
| G | 500 | 250 | 0 | 0 | 12.85 |

[1]Deamidation reactions were maintained for 18 hours at about 20 degrees C and then neutralized (about pH 6.34 to about ph 6.46) by admixture with HCl. Then 9.5 ml PBS was admixed to each sample.
[2]Volumes of reactants are in microliters (ul).
[3]Apo AI/HDL stock was 10 mg/protein per ml.

Fifth microliters of serial 3 fold dilutions of each sample prepared in Table 3 were admixed as competitor in the RIA described in this Example. The mean counts per minute (CPM) of $^{125}$I-labeled solid phase immunoreaction product produced in the presence of each dilution of each sample and the respective B/B$_o$ values are shown in Table 4 below:

TABLE 4

| Competitor Dilution | NaOH Treated Samples | | | | | | | |
|---|---|---|---|---|---|---|---|---|
| | A | | B | | C | | D | |
| | CPM | B/Bo | CPM | B/Bo | CPM | B/Bo | CPM | B/Bo |
| Neat | 965 | 0.099 | 1110 | 0.118 | 1070 | 0.112 | 589 | 0.051 |
| 1:3 | 2542 | 0.301 | 2852 | 0.341 | 2479 | 0.293 | 1174 | 0.126 |
| 1:9 | 4799 | 0.527 | 4399 | 0.540 | 4502 | 0.553 | 2746 | 0.328 |
| 1:27 | 5786 | 0.718 | 6195 | 0.771 | 6005 | 0.746 | 3854 | 0.470 |
| 1:81 | 6745 | 0.841 | 6988 | 0.872 | 6618 | 0.825 | 5220 | 0.645 |
| 1:243 | 7270 | 0.090 | 7483 | 0.936 | 7277 | 0.909 | 6385 | 0.795 |
| 1:729 | 7255 | 0.907 | 7406 | 0.926 | 7485 | 0.936 | 6917 | 0.863 |

| Competitor Dilution | E | | F | | G | | Apo AI/HDL | |
|---|---|---|---|---|---|---|---|---|
| | CPM | B/Bo | CPM | B/Bo | CPM | B/Bo | CPM | B/Bo |
| Neat | 263 | 0.009 | 222 | 0.004 | 195 | 0.000 | 1152 | 0.123 |
| 1:3 | 553 | 0.046 | 185 | −.001 | 305 | 0.016 | 2348 | 0.277 |
| 1:9 | 881 | 0.088 | 281 | 0.011 | 339 | 0.019 | 3778 | 0.460 |
| 1:27 | 1543 | 0.173 | 342 | 0.019 | 497 | 0.039 | 5057 | 0.624 |
| 1:81 | 2283 | 0.268 | 516 | 0.041 | 771 | 0.074 | 5868 | 0.729 |
| 1:243 | 3338 | 0.404 | 744 | 0.071 | 1157 | 0.124 | 6380 | 0.794 |
| 1:729 | 4918 | 0.607 | 1295 | 0.141 | 1891 | 0.218 | 6679 | 0.833 |

[1]B = CPM bound in presence of competitor minus background CPM; Bo = CPM bound in absence of competitor (i.e., 100% binding) minus background CPM.

The results in Table 4 indicate that the epitope recognized by MAB AI-18 is stable to NaOH treatments such as those received by samples B and C, sample A being the no treatment control. Because NaOH treatment causes changes in Apo AI in addition to deamidation, it is believed that the decrease in expression of the epitope recognized by MAB AI-18 observed with samples D, E, F and G was not substantially due to deamidation.

Figure 3A:
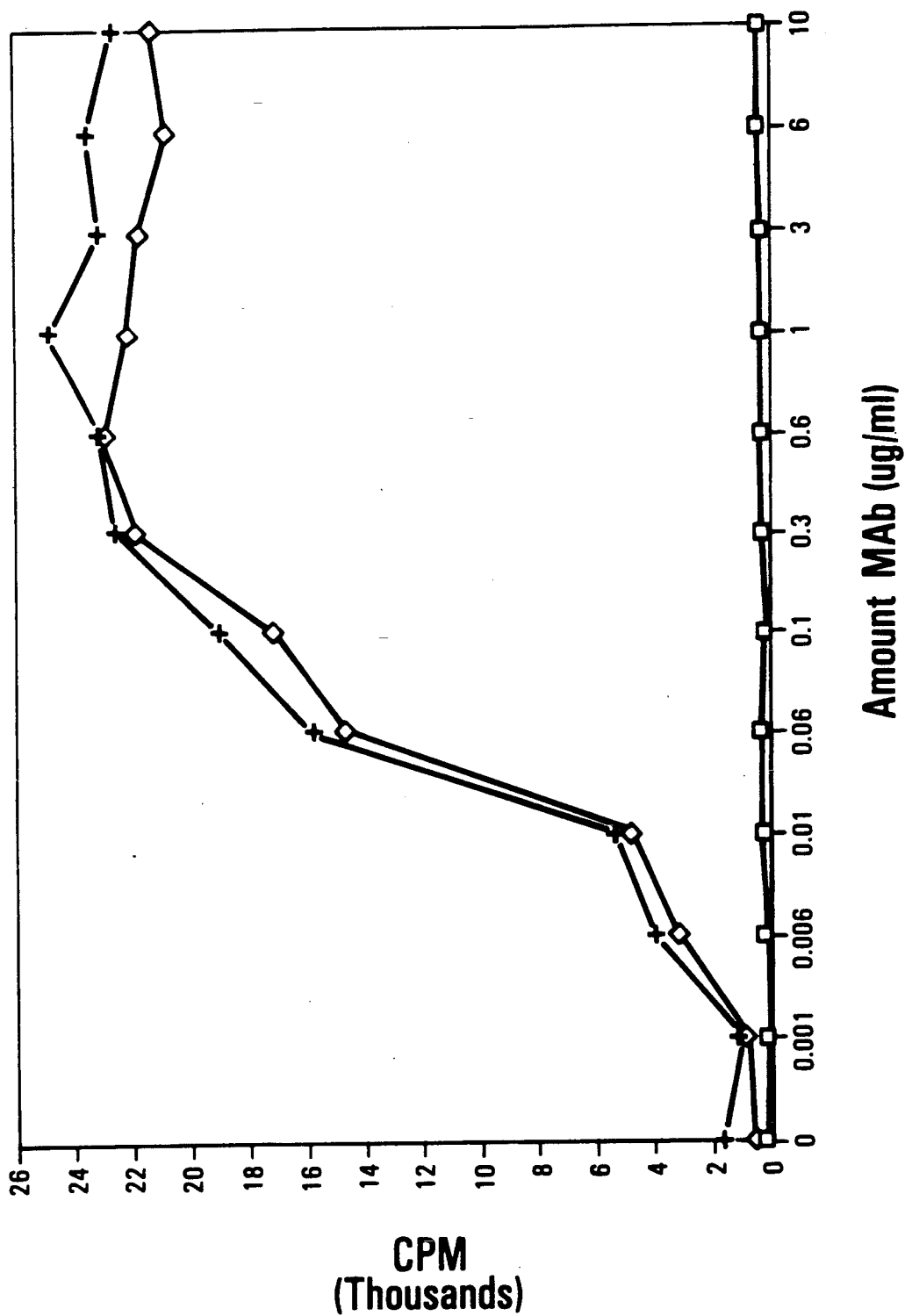
FIG. 3 contains two panels illustrating the ability of MAB AI-18 to immunoreact with Apo AI/HDL (+) and deamidated Apo AI/HDL(◊). Background levels obtained using no antibody at each dilution are also shown (□). In panel 3A, the parallel immunoreactivity of MAB AI-18 for both the amidated and deamidated material indicates the epitope recognized by that antibody is a native conserved epitope. In contrast, panel 3B shows that anti-Apo AI MAB C3.5 recognizes an epitope whose expression is decreased, to the point where it is almost not distinguishable from background, by deamidation.
Figure 3B:
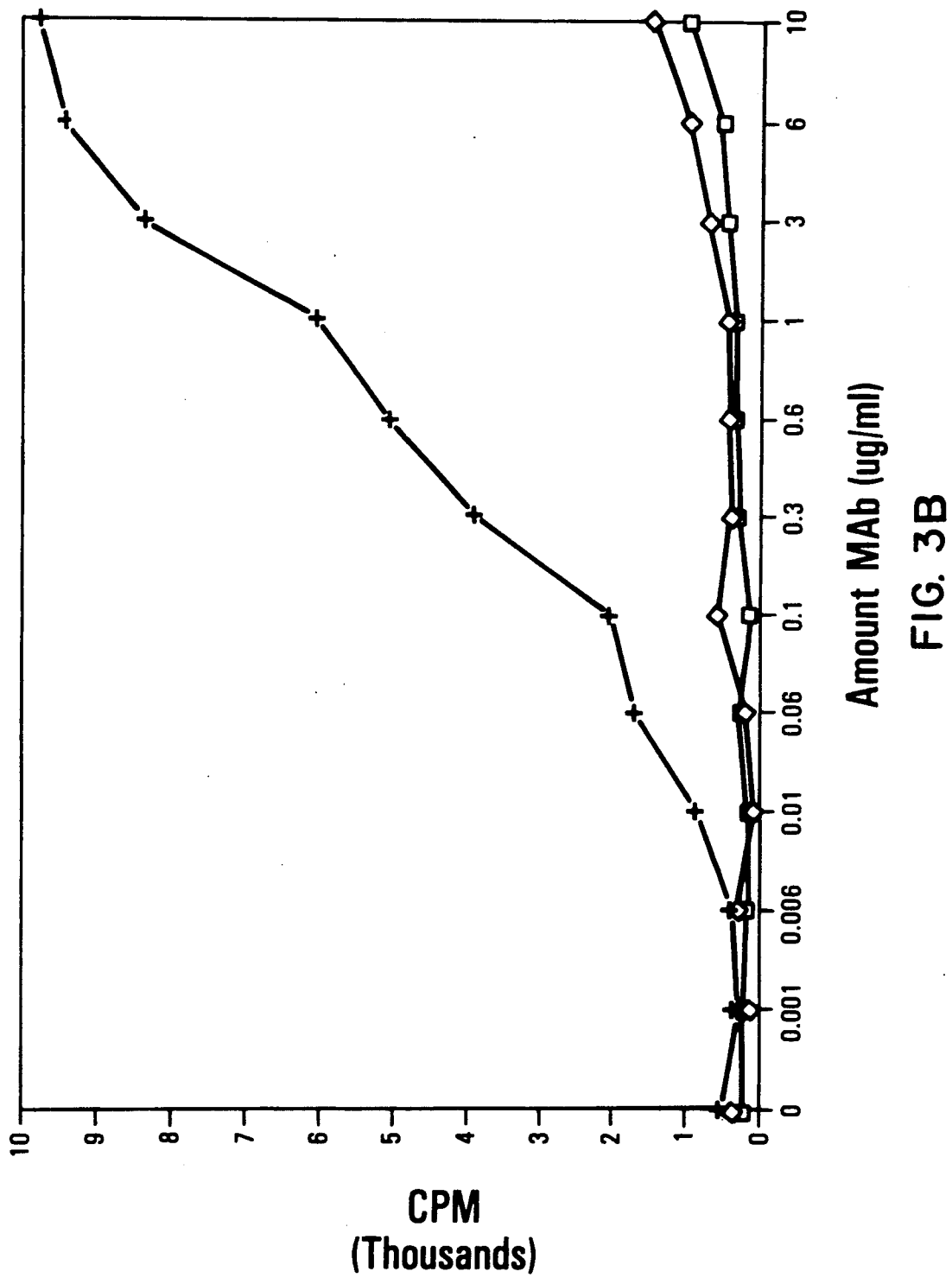
Figure 4:
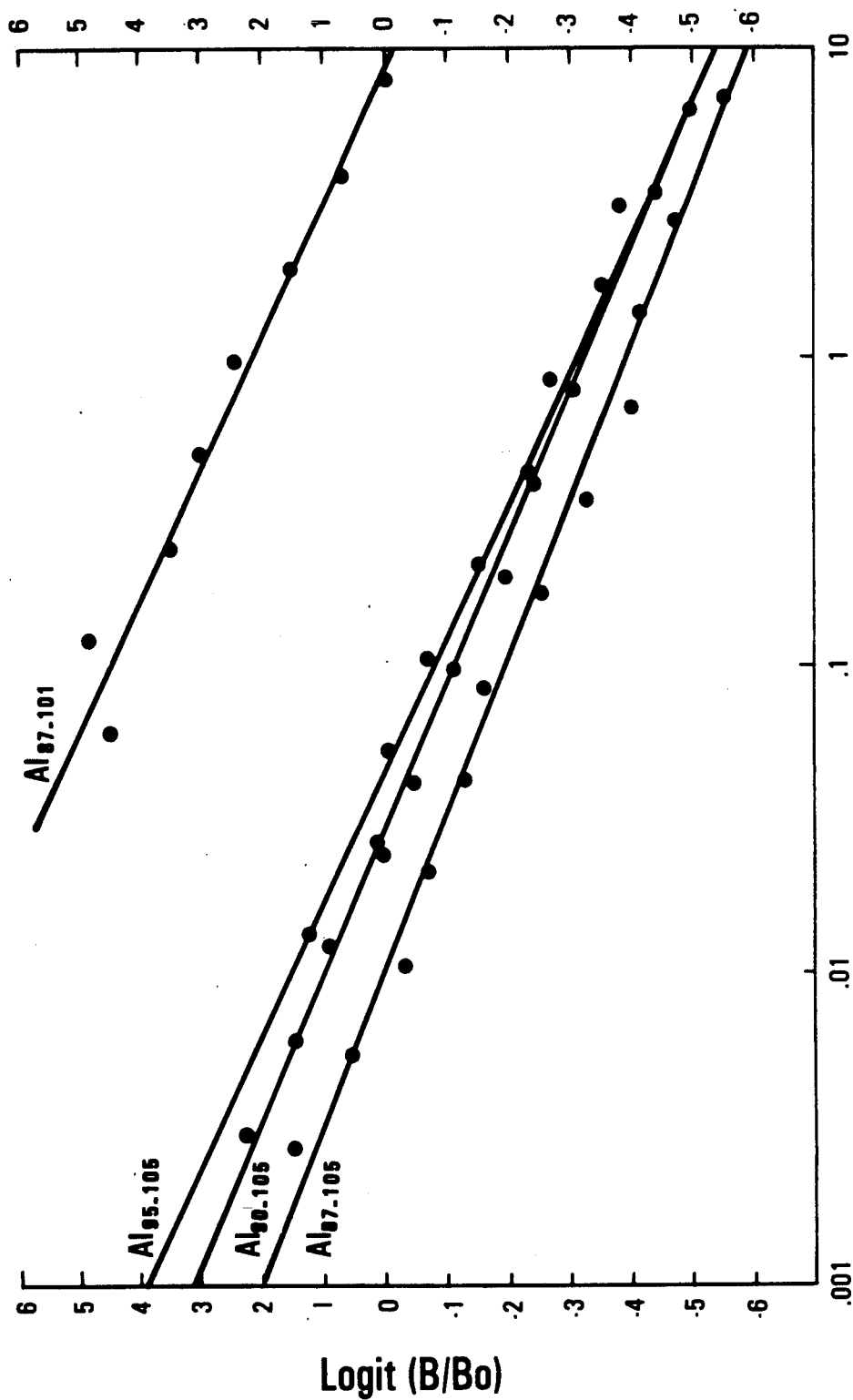
FIG. 4 illustrates the immunoreactivity of MAB AI-18 for peptides AI87-105, AI90-105, AI95-105 and AI87-101. The concentration of peptide competitor is shown in ug protein/ml determined as described in FIG. 2.
Figure 5:
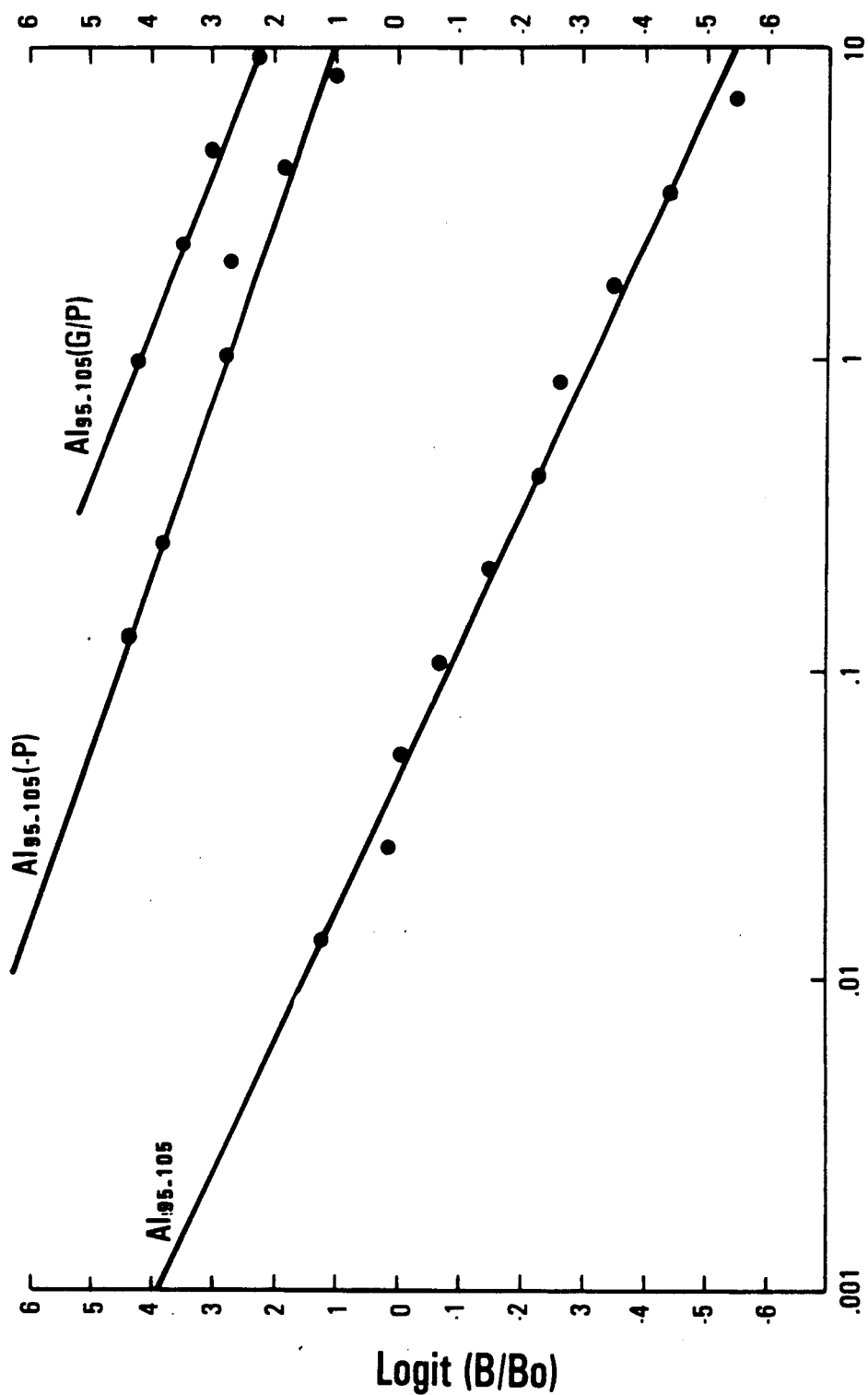
FIG. 5 illustrates the immunoreactivity of MAB AI-18 for peptides AI95-105, AI95-105(-P) and AI95-105(G/P). Peptide concentrations were determined as in FIG. 2. This figure demonstrates that either deleting the proline residue at position 99 [AI95-105(-P)] or substituting glycine for proline at position 99 [AI95-105(G/P)] substantially decreases the ability of the peptide to immunologically mimic a native conserved epitope of the Apo AI.
Figure 6:
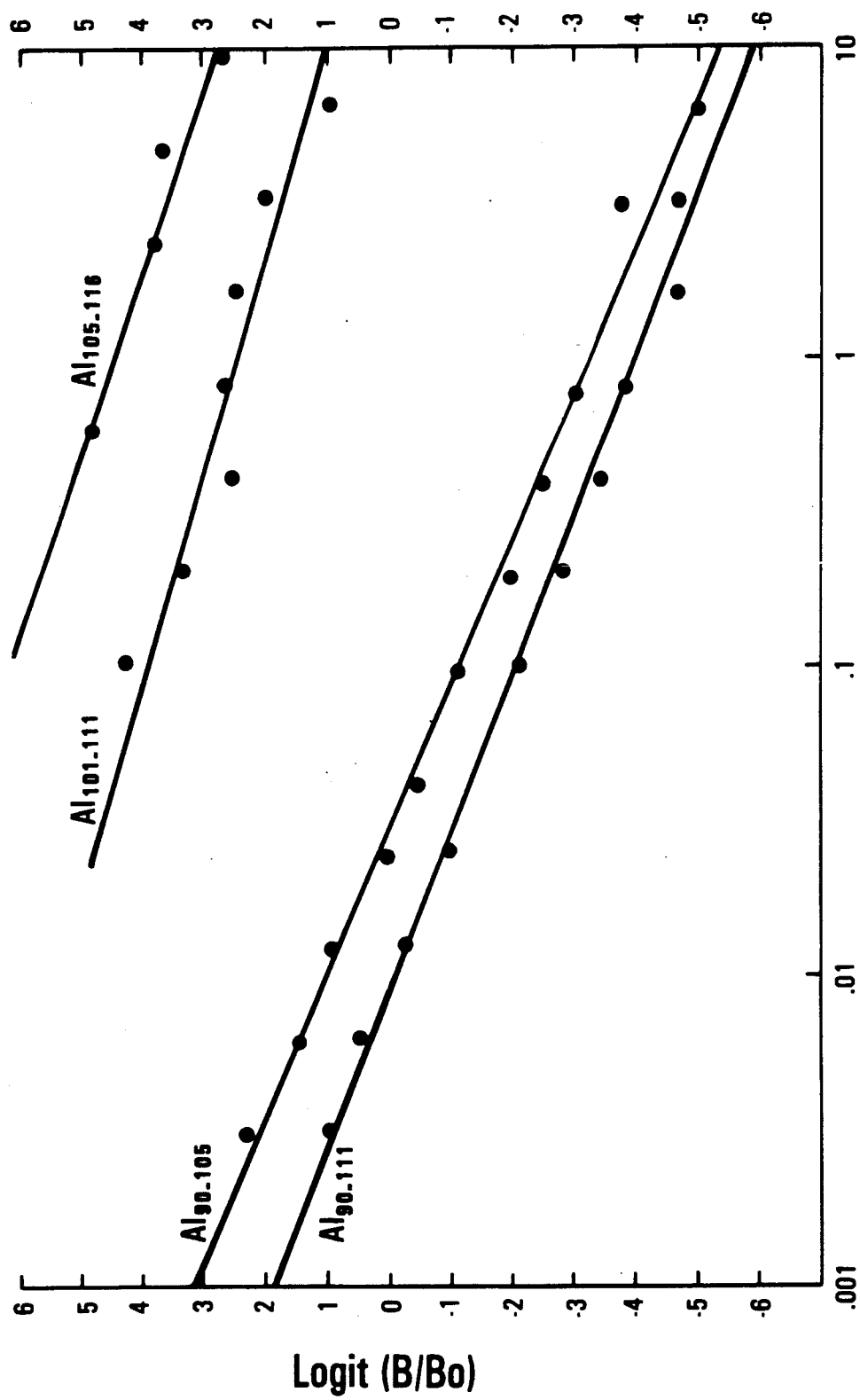
FIG. 6 illustrates the immunoreactivity of MAB Ai-18 for peptides AI101-111 and AI105-116 compared to two peptides of the present invention, i.e., AI90-105 and AI90-111. Peptide concentrations were determined as described in FIG. 2.
Figure 7:
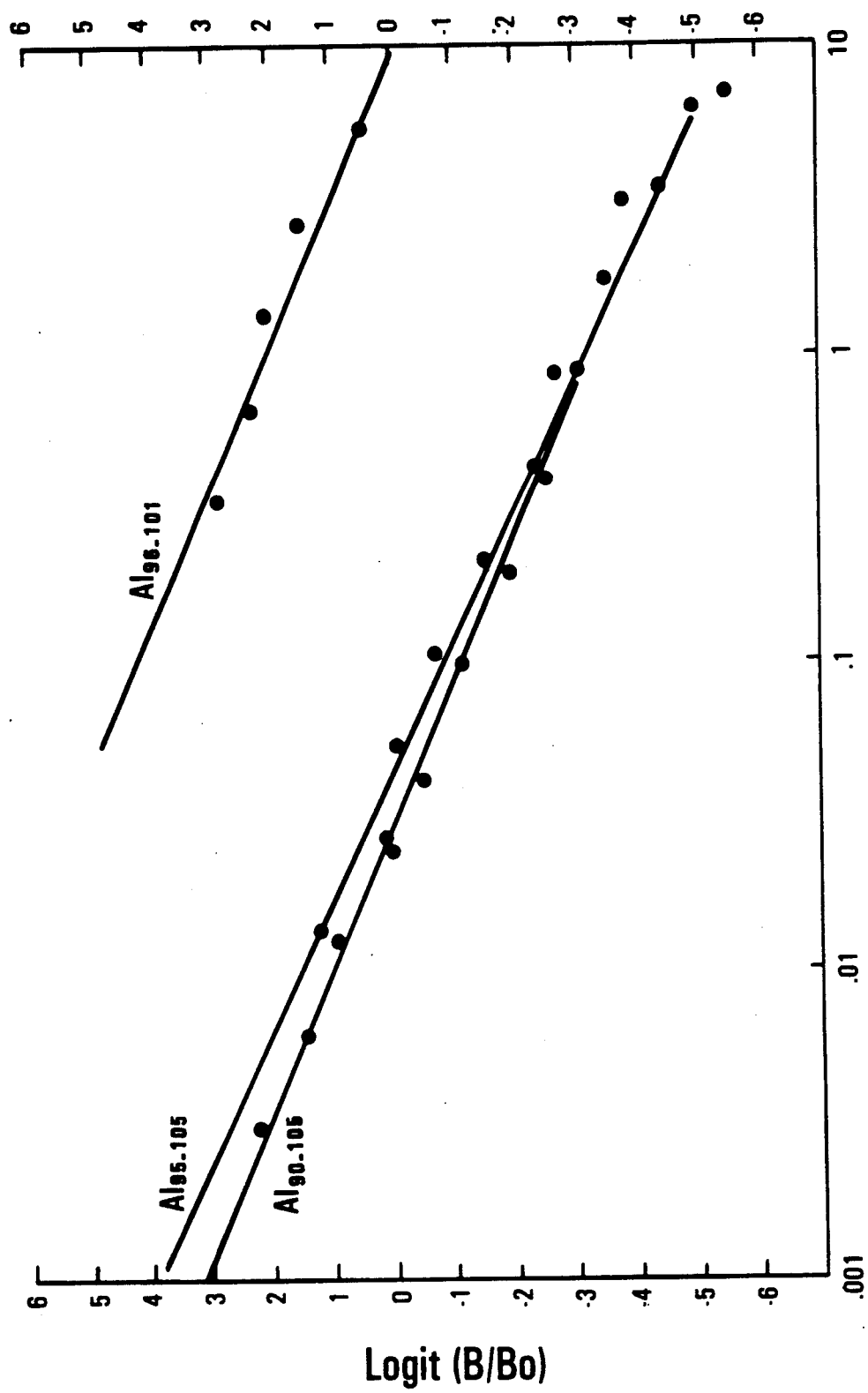
FIG. 7 illustrates the immunoreactivity of MAB AI-18 for peptide AI96-101 compared to peptides AI95-105 and AI90-105. Peptide concentration were determined as described in FIG. 2.

To further examine the stability of MAB AI-18 to immunoreact with deamidated Apo AI/HDL MAB AI-18 and MAB C3.5, another anti-Apo AI monoclonal, were titrated against Apo AI/HDL prepared in a manner similar to sample B above. The results of that study, shown in FIG. 3, indicate that the Apo AI epitope recognized by MAB C.5 is completely degraded by deamidation whereas expression of the epitope recognized by MAB AI-18 is substantially unaffected by deamidation.

To determine the immmunoreactivity of MAB AI-18 for the polypeptides shown in Tables 1 and 2, a stock solution of each was prepared at a concentration of 10 ug/ml. Fifty microliters of the stock of 2 fold serial dilutions of the stock were used as competitor in the RIA described in this Example. The results of this study are graphically illustrated in FIGS. 3-6 and summarized in Table 5 below:

TABLE 5

| Peptide Competitor | Immunoreactivity[1] |
|---|---|
| AI90-105 | 30 |
| AI90-111 | 9 |
| AI87-105 | 10 |
| AI95-105 | 45 |
| AI87-101 | 8,400 |
| AI93-101 | >10,000 |
| AI105-116 | >10,000 |
| AI101-111 | >10,000 |
| AI100-105 | >10,000 |
| AI103-101 | >10,000 |
| AI96-101 | >10,000 |
| AI95-105 (-P) | >10,000 |
| AI95-105 (G/P) | >10,000 |

[1]Immunoreactivity is the concentration in ug protein/ml of peptide competitor required to achieve a B/B$_o$ value of 0.5 in the RIA of this example. It should be noted that a higher immunoreactivity value represents a lower affinity for the antibody-antigen reaction.

The above results indicate that MAB AI-18 displays equivalent immunoreactivities for peptides AI90-105, AI90-111, AI87-105 and AI95-105, i.e., the ratio of the immunoreactivities in the range of 1:5 to 5:1.

In addition, a comparison of the immunoreactivity of MAB AI-18 for AI95-105, AI95-105 (-P) and AI95-105 (G/P) indicates that the presence of proline at position 99 is required for expression by a peptide of the conserved Apo AI-epitope recognized by MBA AI-18. The high immunoreactivity values for peptides AI105-116, AI101-111, AI100-105, AI87-101 and AI93-101, which either do not contain proline or do not contain proline flanked by at least four amino acid residues on both sides, suggest that for a peptide to be capable of immunologically mimicking the Apo AI-epitope recognized by MAB AI-18 it must have at least about 10 amino acid residues corresponding in sequence to the Apo AI sequence in the region of residue positions 90–105 and that it must contain a proline flanked on both sides by at least about four residues.

7. Solid-Phase Polypeptide Competitive ELISA

Six hundred microliters of 25 mM $NH_4HCO_3$, pH 9.6, containing polypeptide AI90-105 at a concentration of 5 mg/ml were admixed with 119.4 ml of 0.1M $NaHC)_3$, pH 9.0, to form a peptide coating solution. One hundred fifty microliters of the coating solution were admixed into the wells of flexible polyvinyl chloride microtiter plates (Nunc, Source). The wells were then maintained about 16-20 hours at 4 degrees C. to permit the peptide to adsorb onto (coat) the walls of the wells. After removing the peptide coating solution by shaking, the wells were washed once with 350 ul of rinsing buffer (PBS containing 1 gm/l BSA, 0.5 ml/l Tween 20, and 2 ul/l aprotinin). Excess protein binding sites were blocked by admixing 200 ul of blocking buffer (PBS containing 3% BSA) into each well, maintaining the wells for 1 hour at 20 degrees C., removing the blocking buffer by shaking, and then washing the wells 3 times as previously described. The AI90-105 polypeptide-containing solid supports thus formed were stored in the presence of a desiccant at 4 degrees C. until used.

One hundred microliters of a sample or standard to be assayed were admixed into a polypeptide-coated well. Subsequently, 100 ul of PBS containing 0.5 ug/ml HPPO-labeled MAB AI-18 were admixed into each well. The resulting solid-liquid phase competitive immunoreaction admixture was maintained at 20 degrees C. for 60 minutes to permit formation of a liquid-phase Apo AI-containing immunoreaction product and a solid-phase polypeptide-containing immunoreaction product. The wells were then washed 3 times with rinsing buffer to separate the solid-and liquid-phase products.

Two hundred microliters of OPD substrate were then admixed into each well to form a developing-reaction admixture, which was maintained for 30 minutes at about 20 degrees C. Subsequently, 50 ul of 4N $H_2SO_4$ were admixed into each well to stop the developing-reaction, and the resulting solution were assayed for absorbance at 490 nanometers using a microtiter plate reader (Dynatech).

Figure 8:
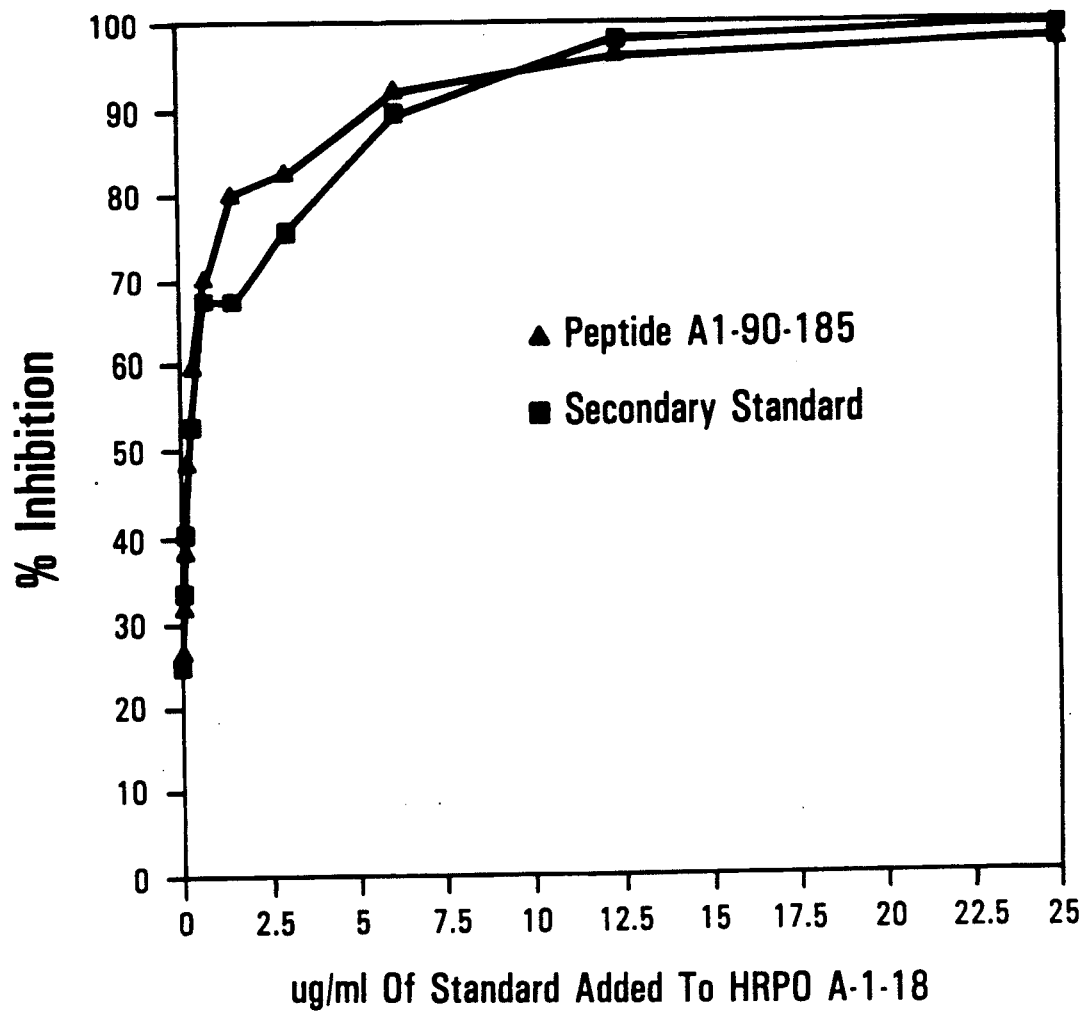
FIG. 8 illustrates the use of a diagnostic system of the present invention to generate a standard curve using the various indicated concentrations of peptide AI90-105 (▲) as competitive inhibitor. A standard curve using pooled normal plasma as a reference material (■) was also used to generate a standard curve.

The above solid-phase ELISA was used to compare the abilities of polypeptide AI90-105 and an Apo AI reference material to compete for binding to MAB AI-18. The reference material was a pool of about 20 normal plasmas having a known amount of assayable Apo AI/HDL. The results of that study, shown in FIG. 8, indicate that MAB AI-18 has equivalent immunoreactivities for the peptide and the reference material.

The foregoing specification, including the specific embodiments and examples, is intended to be illustrative of the present invention and is not to be taken as limiting. Numerous other variations and modifications can be effected without departing from the true spirit and scope of the present invention.

What is claimed is:

1. An Apo AI polypeptide consisting essentially of no more than 25 amino acid residues and having as a part of its amino acid residue sequence a sequence represented by the formula:

—AKVQPYLDDFQ—

2. The polypeptide of claim 1 wherein said polypeptide has an amino acid residue sequence represented by a formula selected from the group consisting of:
   (a) AKVQPYLDDFQ,
   (b) LEEVKAKVQPYLDDFQ,
   (c) LEEVKAKVQPYLDDFQKKWQEE, and
   (d) SKDLEEVKAKVQPYLDDFQ.

3. A monoclonal antibody containing anti-Apo AI antibody molecules that immunoreact with:
   (a) Apo AI/HDL.
   (b) isolated Apo AI
   (c) deamidated Apo AI/HDL
   (d) Apo AI CNBr2, and
   (e) the polypeptide LEEVKAKVQPYLDDFQ,
but do not immunoreact with:
   (f) Apo AI CNBr1,
   (g) Apo AI CNBr3,
   (h) Apo AI CNBr4,
   (i) the polypeptide LEEVKAKVQYLDDFQ, and
   (j) the polypeptide LEEVKAKVQGYLDDFQ.

4. The monoclonal antibody of claim 3 wherein said antibody molecules are those produced by the hybridoma having ATCC designation HB9570.

5. A diagnostic system, in kit form, comprising, in an amount sufficient to perform at least one assay, an Apo AI polypeptide represented by a formula selected from the group consisting of:
   (a) AKVQPYLDDFQ,
   (b) LEEVKAKVQPYLDDFQ,
   (c) LEEVKAKVQPYLDDFQKKWQEE, and
   (d) SKDLEEVKAKVQPYLDDFQ.

6. The diagnostic system of claim 5 wherein said polypeptide is operatively linked to a solid matrix.

7. The diagnostic system of claim 5 further comprising, in an amount sufficient to perform at least one assay, a monoclonal antibody containing anti-Apo AI antibody molecules that immunoreact with:
   (a) Apo AI/HDL
   (b) isolated Apo AI
   (c) deamidated Apo AI/HDL
   (d) Apo AI CNBr2, and
   (e) the polypeptide LEEVKAKVQPYLDDFQ,
but do not immunoreact with:
   (f) Apo AI CNBr1,
   (g) Apo AI CNBr3,
   (h) Apo AI CNBr4,
   (i) the polypeptide LEEVKAKVQYLDDFQ, and
   (j) the polypeptide LEEVKAKVQGYLDDFQ.

8. The diagnostic system of claim 7 wherein said antibody molecules are those produced by the hybridoma having ATCC designation HB9570.

9. The diagnostic system of claim 7 wherein said antibody molecules are operatively linked to an enzyme indicating means.

10. A diagnostic system, in kit form, comprising, in an amount sufficient to perform at least one assay, a monoclonal antibody containing anti-Apo AI antibody molecules that immunoreact with:
    (a) Apo AI/HDL
    (b) isolated Apo AI
    (c) deamidated Apo AI/HDL
    (d) Apo AI CNBr2, and
    (e) the polypeptide LEEVKAKVQPYLDDFQ,
but do not immunoreact with:
    (f) Apo AI CNBr1,
    (g) Apo AI CNBr3,
    (h) Apo AI CNBr4,
    (i) the polypeptide LEEVKAKVQYLDDFQ, and
    (j) the polypeptide LEEVKAKVQGYLDDFQ.

11. The diagnostic system of claim 10 wherein said antibody molecules are those capable of being produced by the hybridoma having ATCC designation HB9570.

12. The diagnostic system of claim 11 wherein said antibody molecules are operatively linked to an enzyme indicating means.

13. A method of assaying the amount of Apo AI in a vascular fluid sample comprising the steps of:
    (a) forming an immunoreaction admixture by admixing a vascular fluid sample with:
        (i) an anti-Apo AI monoclonal antibody produced by the hybridoma having ATCC designation HB9570, and
        (ii) an Apo AI polypeptide selected from the group consisting of:
            (a) AKVQPYLDDFQ,
            (b) LEEVKAKVQPYLDDFQ,
            (c) LEEVKAKVQPYLDDFQKKWQEE, and
            (d) SKDLEEVKAKVQPYLDDFQ;
    (b) maintaining said immunoreaction admixture for a time period sufficient to form an Apo AI-containing immunoreaction product, and
    (c) determining the amount of product formed in step (b).

14. The method of claim 13 wherein said polypeptide is operatively linked to a solid-matrix, said antibody is operatively linked to an enzyme label, and said product formed in step (b) is a labeled immunoreaction product.

15. A hybridoma that produces antibody molecules capable of immunoreacting with Apo AI/HDL and the polypeptide LEEVKAKVQPYLDDFQ, and has the ATCC designation HB9570.

* * * * *

UNITED STATES PATENT AND TRADEMARK OFFICE
CERTIFICATE OF CORRECTION

PATENT NO. : 5,055,396  Page 1 of 1
DATED : October 8, 1991
INVENTOR(S) : Linda K. Curtiss and Richard S. Smith It is certified that error appears in the above-identified patent and that said Letters Patent is hereby corrected as shown below:

<u>Column 1,</u>
Line 6, insert,
-- This invention was made with government support under Grant No. HL 14197 from the National Institutes of Health. The government may have certain rights in the invention. --

Signed and Sealed this

Fourth Day of March, 2003

JAMES E. ROGAN
*Director of the United States Patent and Trademark Office*